United States Patent [19]
Lo et al.

[11] Patent Number: 5,738,104
[45] Date of Patent: Apr. 14, 1998

[54] EKG BASED HEART RATE MONITOR

[75] Inventors: Thomas Ying-Ching Lo, Fremont, Calif.; Yuh Snow Tsai, Nashville, Tenn.

[73] Assignee: Salutron, Inc., Hayward, Calif.

[21] Appl. No.: 554,373

[22] Filed: Nov. 8, 1995

[51] Int. Cl.$^6$ .......................... A61B 5/04; A61B 5/0402; A61B 5/0404
[52] U.S. Cl. ........................... 128/706; 128/707
[58] Field of Search ....................... 128/706, 707

[56] References Cited

U.S. PATENT DOCUMENTS

| | | |
|---|---|---|
| 3,212,496 | 10/1965 | Preston . |
| 3,218,638 | 11/1965 | Honig . |
| 3,648,688 | 3/1972 | O'Hanlon et al. . |
| 3,688,776 | 9/1972 | Kenny . |
| 3,702,113 | 11/1972 | Blockley ........................ 128/707 |
| 3,704,706 | 12/1972 | Herczfeld et al. . |
| 3,767,195 | 10/1973 | Dimick . |
| 3,769,974 | 11/1973 | Smart et al. . |
| 3,796,213 | 3/1974 | Stephens . |
| 3,807,388 | 4/1974 | Orr et al. . |
| 3,923,041 | 12/1975 | Stasz et al. . |
| 3,949,388 | 4/1976 | Fuller . |
| 3,978,848 | 9/1976 | Yen et al. . |
| 3,993,047 | 11/1976 | Peek . |
| 4,038,976 | 8/1977 | Hardy et al. . |
| 4,052,979 | 10/1977 | Scherr et al. . |

(List continued on next page.)

FOREIGN PATENT DOCUMENTS

| | | |
|---|---|---|
| 2-126829 | 5/1990 | Japan . |
| 2-126148 | 4/1991 | Japan . |
| 3-086148 | 4/1991 | Japan . |
| 5-076500 | 3/1993 | Japan . |
| 5-076501 | 3/1993 | Japan . |
| 0611701 | 2/1994 | Japan . |
| 2165352 | 4/1986 | United Kingdom ............... 128/707 |

OTHER PUBLICATIONS

"Nonlinear Transforms of ECG Signals for QRS Detection: A Quantitative Analysis", S. Suppappola, Y. Sum, IEEE Transactions on Biomedical Engineering, vol. 41, No. 4, Apr. 1994 pp. 397–399.

"Microcontroller–Based Real–Time QRS Detection", S. Ying, S. Suppappola, T. Wrublewski, Biomedical Instrumentation and Technology, vol. 26, No. 6, Nov–Dec. 1992, pp. 477–484.

"Quantitative Investigation of QRS Detection Rules Using the MIT/BIH Arrhythmia Database", P. Hamilton & W. Tompkins, IEEE Transactions on Biomedical Engineerin, vol. BME-33, No. 12, Dec. 1986, pp. 1157–1165.

"A Fast Band-pass Filter for ECG Processing", T.Y. Lo & P.C. Tang, Proceedings–Fourth Annual Conference, IEEE Engineering in Medicine and Biology Society, pp. 321–325, Sep. 1982.

*Primary Examiner*—William E. Kamm
*Assistant Examiner*—Carl H. Layno
*Attorney, Agent, or Firm*—Townsend and Townsend and Crew LLP

[57] ABSTRACT

A heart rate monitor for calculating heart rate based upon EKG signals. The monitor preferably utilizes 3 electrodes to pick up EKG signals and a differential amplifier to cancel common mode signals in the output of the electrode. An analog bandpass filter comprised of a low pass and high pass filter in series each with different rolloffs filters out low and high frequency components. The signals are digitized and digital filtering to remove power line hum and remnants of low and high frequency noise is performed. Then the EKG signals are digitally enhanced by differentiating and squaring the results of the differentiator then being averaged in a moving average computation so as to generate enhanced digital data. The enhanced digital data is then processed to learn the EKG characteristics, and a heart rate arbitrator processes the incoming signals to select out actual EKG complexes from EMG noise and other noise. The EKG isolation process is done using rules of reason and the learned characteristics of the EKG signal.

24 Claims, 19 Drawing Sheets

U.S. PATENT DOCUMENTS

| | | | |
|---|---|---|---|
| 4,054,779 | 10/1977 | Wilke . | |
| 4,063,551 | 12/1977 | Sweeney . | |
| 4,083,366 | 4/1978 | Gombrich et al. . | |
| 4,096,854 | 6/1978 | Perica et al. . | |
| 4,105,020 | 8/1978 | Matsuoka et al. . | |
| 4,120,294 | 10/1978 | Wolfe . | |
| 4,129,124 | 12/1978 | Thalmann . | |
| 4,163,447 | 8/1979 | Orr . | |
| 4,166,454 | 9/1979 | Meijer . | |
| 4,185,621 | 1/1980 | Morrow . | |
| 4,195,642 | 4/1980 | Price et al. . | |
| 4,221,223 | 9/1980 | Linden . | |
| 4,224,948 | 9/1980 | Cramer et al. . | |
| 4,230,127 | 10/1980 | Larson . | |
| 4,248,244 | 2/1981 | Charnitski et al. | 128/706 |
| 4,256,117 | 3/1981 | Perica et al. . | |
| 4,280,506 | 7/1981 | Zurcher . | |
| 4,295,472 | 10/1981 | Adams . | |
| 4,301,808 | 11/1981 | Taus . | |
| 4,305,401 | 12/1981 | Reissmueller et al. . | |
| 4,307,728 | 12/1981 | Walton . | |
| 4,319,581 | 3/1982 | Cutter . | |
| 4,331,154 | 5/1982 | Broadwater et al. . | |
| 4,353,152 | 10/1982 | O'Connor et al. . | |
| 4,358,105 | 11/1982 | Sweeney, Jr. . | |
| 4,406,298 | 9/1983 | Walbeoffe-Wilson et al. . | |
| 4,407,295 | 10/1983 | Steuer et al. . | |
| 4,409,983 | 10/1983 | Albert . | |
| 4,412,546 | 11/1983 | Barthels . | |
| 4,420,000 | 12/1983 | Bailey | 128/706 |
| 4,425,921 | 1/1984 | Fujisaki et al. . | |
| 4,450,001 | 5/1984 | Ewing . | |
| 4,464,123 | 8/1984 | Glover et al. . | |
| 4,478,225 | 10/1984 | Ewing . | |
| 4,517,986 | 5/1985 | Bilgutay . | |
| 4,572,207 | 2/1986 | Yoshimi et al. | 128/706 |
| 4,573,478 | 3/1986 | Arnold et al. . | |
| 4,625,733 | 12/1986 | Saynajakangas . | |
| 4,641,658 | 2/1987 | Lepper . | |
| 4,667,682 | 5/1987 | Ihlenfeld, III | 128/706 |
| 4,753,243 | 6/1988 | Mawhinney et al. . | |
| 4,819,868 | 4/1989 | Hargrove et al. . | |
| 4,834,532 | 5/1989 | Yount . | |
| 4,868,759 | 9/1989 | Kahn et al. . | |
| 4,883,055 | 11/1989 | Merrick . | |
| 4,905,704 | 3/1990 | Walloch . | |
| 4,909,259 | 3/1990 | Tehrani . | |
| 4,938,228 | 7/1990 | Righter et al. | 128/706 |
| 5,003,983 | 4/1991 | Dingwell et al. . | |
| 5,094,244 | 3/1992 | Callahan et al. . | |
| 5,100,374 | 3/1992 | Kagayama . | |
| 5,156,147 | 10/1992 | Warren et al. . | |
| 5,215,097 | 6/1993 | Watabe . | |
| 5,228,449 | 7/1993 | Christ et al. . | |
| 5,243,992 | 9/1993 | Eckerle et al. . | |
| 5,243,993 | 9/1993 | Alexander et al. | 128/706 |
| 5,261,414 | 11/1993 | Aung et al. . | |
| 5,297,557 | 3/1994 | Reichl | 128/707 |
| 5,314,389 | 5/1994 | Dotan . | |
| 5,318,487 | 6/1994 | Golen et al. . | |
| 5,323,784 | 6/1994 | Shu . | |
| 5,365,934 | 11/1994 | Leon et al. . | |
| 5,394,879 | 3/1995 | Gorman . | |
| 5,400,794 | 3/1995 | Gorman . | |
| 5,406,952 | 4/1995 | Barnes et al. . | |
| 5,417,716 | 5/1995 | Franberg et al. . | |
| 5,431,178 | 7/1995 | Mathews . | |
| 5,503,160 | 4/1996 | Pering et al. | 128/706 |

$$Y_N = \frac{1}{8}(2Y_{N-1} - Y_{N-2} + X_N - 2X_{N-3} + X_{N-6})$$

FIG. 13.

$$Y_N = \frac{1}{12}(2Y_{N-1} - 3Y_{N-2} + 2Y_{N-3} - Y_{N-4} + X_N - 2X_{N-6} + X_{N-12})$$

FIG. 14.

$$Y_N = \frac{(2X_N + X_{N-1} - X_{N-3} - 2X_{N-4})}{4}$$

FIG. 15.

$$Y_N = \frac{1}{64}\sum_{i=0}^{7} X_{N-i}$$

FIG. 16.

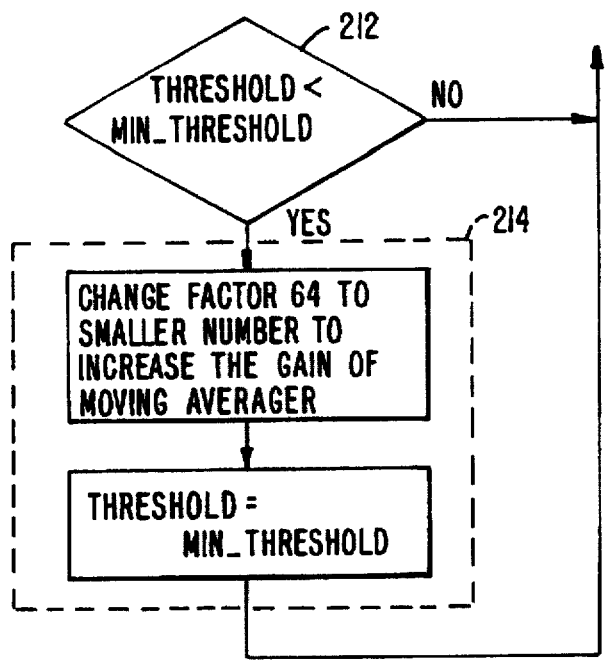
FIG. 26.
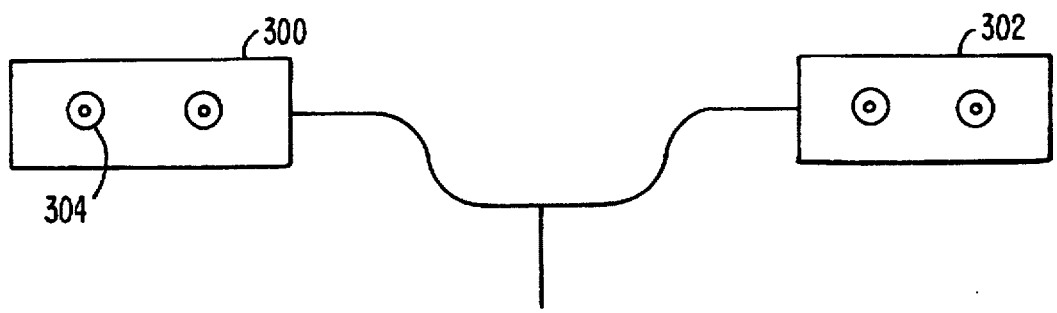
FIG. 27.
FIG. 28.
FIG. 29.

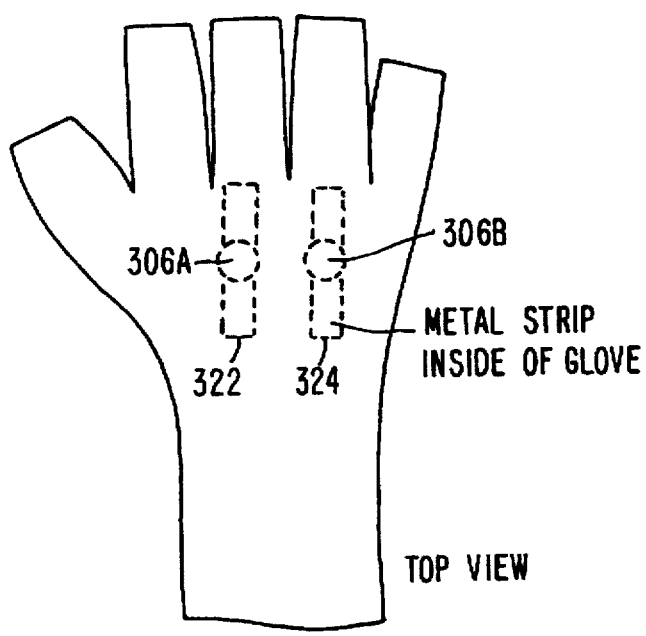
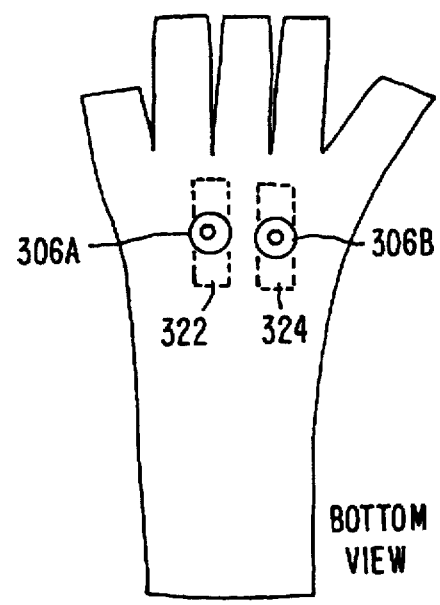
FIG. 30A.
FIG. 30B.

EKG BASED HEART RATE MONITOR

FIELD OF THE INVENTION

The invention pertains to the field of pulse monitors, and, more particularly, to the field of pulse monitors that use EKG signals to detect the pulse rate.

BACKGROUND ART

In the prior art, two basic types of pulse rate monitors exist. The first type uses visible or infrared radiation which is projected through the skin to detect from radiation reflected from or penetrated through capillaries under the skin, pulsations of blood flow. Typically, these devices come in the form of a digital watch such as Casio or Timex with a photodetector on the face of the watch or as a desktop unit or unit that clips to a belt with a clip connected to base unit, the clip for attaching to a fingertip or earlobe. Visible or infrared light passing through the skin is detected by the photodetector and gives an indication of pulsations in blood flow in capillaries. From these pulsations, the pulse rate is calculated.

Numerous examples of this type pulse monitor exist as they are commonly found on fitness equipment such as treadmills, stationary bicycles and stairmasters. Another example of this type system is a pulse rate monitor wrist watch made by Casio. This watch reads both blood pressure and pulse. The watch has two sensors on top of the watch. The sensor on the lower left of the face of the watch is a photosensor which is to be covered with the wearer's right index finger. The other sensor is to be covered by the right middle finger and is an electrode to pick up the EKG signals. The bottom plate of the watch body serves as the other electrode.

There are several disadvantages to the photosensor/flow pulsation detectors. First, the finger position on the photosensor must be stable. Also, the force pressing the finger or ear lobe to the photodetector must be nominal. If the force is too high, the blood flow will be cut off, and no detection of blood flow pulsations can occur. If the force is too low, then any slight motion between the body and the sensor may cause inaccurate readings. Also, the reliability of the readings depends upon the ambient illumination (unless a separate photodiode supplies light for transmission through the skin) and upon the wavelength. Further, the flow pulse in a capillary looks like a sinusoidal waveform in shape. This makes it difficult to distinguish legitimate flow pulse signals from sinusoidally shaped noise waveforms. A digital watch employing these principles manufactured by Timex has been discontinued because of poor performance.

The second type of pulse rate monitor is the EKG type. These type pulse monitors work by picking up an EKG signal from the heart muscle itself and calculating the pulse rate from the EKG signal. One example of this type system is a pulse rate monitor wrist watch made by Casio. This watch reads both blood pressure and pulse. The watch has two sensors on top of the watch. The sensor on the lower left of the face of the watch is a photosensor which is to be covered with the wearer's right index finger and which detects fluctuations in light passing through the finger from ambient sources to determine when blood flow pulses occur. The sensor on the lower right of the face is one of two sensors for an EKG signal. The bottom surface of the watch is the other sensor for picking up the EKG signal. To use this watch to read blood pressure and pulse, the user must first use another independent instrument to measure blood pressure and pulse in an at-rest condition. These readings are then input to the watch. After inputting this data, the watch takes about 10–20 heartbeats with the user's fingers in contact with the two contacts on the face of the watch. During these 10–20 heartbeats, the watch learns the timing between the EKG signals picked up by the EKG contacts and the corresponding blood flow pulses in an at-rest condition. This timing serves as a reference for determination of blood pressure. The operative principle is determination by the watch of the timing between the EKG signal that causes the left ventricle to pump blood to the resulting pulse of blood flow detected by the photodetector in the capillaries of the wearer's fingertip.

A drawback of this design is that the timing between the EKG pulse and the blood flow pulse changes with fitness level as the aerobic effect takes over and new blood flow paths are formed in the body. As a result, the manufacturer recommends that the basic at-rest data read from an independent instrument be updated every three months. This is inconvenient unless the owner of the watch also owns independent instruments to measure blood pressure and pulse rate. Further, the watch is incapable of measuring only pulse rate without also measuring blood pressure. Another example of EKG type system are products that use chest straps with electrodes properly oriented on the chest strap that pick up the EKG signal directly from the heart muscle. The EKG signal is mixed with a carrier and transmitted to a counting unit worn, for example, on a belt clip or as a digital watch. The mixer and transmitter are located on the chest strap, and transmission is by frequency modulation or any other type of modulation of the carrier by the EKG signal. Batteries are required for both the receiver and transmitter. This approach is costly and inconvenient to the user.

Another example of an EKG type pulse monitor is found in U.S. Pat. No. 4,425,921 to Fujisaki et al. This system uses a chest strap having three EKG type contacts arranged in a line that extends across the front chest area of the wearer. These contacts must make good electrical contact with the chest of the wearer. The strap must be placed so that the center contact makes contact with the chest directly over the heart. The two remaining contacts then contact the chest on either side of the heart. This can be a problem for female athletes depending upon the relative position of their hearts to their left breasts. Further, it is inconvenient for female athletes to put the chest strap on and remove it in public.

The three EKG contacts are coupled to a differential amplifier which uses common mode rejection to help remove common mode noise picked up by both contacts on either side of the center contact. The differential amplifier 26 is coupled to a waveform shaping filter 27. The output of the filter is applied to a comparator, and the output of the comparator is coupled to a microcomputer which counts the two intervals between every three heartbeats and calculates therefrom the pulse rate. The microcomputer supposedly executes various calculations, comparisons and judgments of an unspecified nature in accordance with an undisclosed program to avoid the effects of noise or to ignore an abnormally abrupt fluctuation in heart rate. The heart rate so calculated is then displayed.

The Fujisaki et al. device also discloses using a fingertip clip to detect blood flow pulses as a backup sensor front end for the microcomputer. A switch alternately connects the fingertip sensor or the EKG probes to the microcomputer.

An alternative approach to EKG type pulse monitors is represented by U.S. Pat. No. 4,625,733. In this reference, a pulse rate monitor is taught which measures heartbeat and ECG signals and then sends the data from a separate transmitter to a receiver located elsewhere on the body by a form of telemetry. The particular form of telemetry used is through electromagnetic fields. The EKG pickup picks up signals using two input terminals and these signals are amplified by a power amplifier which drives a magnetic coil with current that varies with the EKG signal. A remote receiver picks up these magnetic variations through magnetic coils coupled to a preamplifier and a signal amplifier. A microcomputer then analyzes the received signal and derives a pulse count therefrom.

An interesting example of a more sophisticated approach to EKG type pulse monitors is exemplified by U.S. Pat. No. 5,365,934 owned by Life Fitness. One of the major problems in isolating a heart rate signal using an EKG signal is separating out the true EKG signal from the noise. All EKG probes pick up noise some of which is from the environment and some of which is generated by the body itself. In particular, there is 60 Hertz noise which is picked up from power lines and adjacent AC powered circuitry, and there is also so-called EMG noise. EMG noise is noise generated by the electrical signals that control contractions of muscles such as leg muscles of an athlete who is running or working out on a stairmaster machine. Another kind of noise is caused by loose contact between the electrodes and the skin which changes the impedance of this contact erratically.

EMG noise is particularly troublesome in EKG pulse monitors because its frequency is in the same range as the frequency as the sought after EKG signal. Therefore, special signal processing must be accomplished to separate EMG noise from the desired EKG signal. One type of signal processing methodology that has been tried in the prior art is autocorrelation as exemplified in U.S. Pat. No. 5,365,934. In this patent, the EKG signal is sensed by probes which are typically mounted on the handles of exercise equipment which the user grabs while exercising. The signals sensed by these probes, which contain the EKG signal, are passed through an autocorrelator which performs a correlation calculation between a piece of the signal represented by one buffer's worth of digital samples and an adjacent portion of the signal in time represented by another set of samples. Signal indication logic monitors the output of the autocorrelator for the presence of a periodic signal and generates a synthetic candidate heart rate signal that has the same frequency as the periodic signal in the output of the autocorrelator. The difficulty with this approach is that the EMG signals are also periodic and will cause peaks in the autocorrelator output that do not represent periodic EKG signal. In one embodiment, the signal indication logic has logic which detects a pulse in the autocorrelation signal which has a waveform characteristic of a heartbeat. One way this is done is to pass the output of the autocorrelation function through a filtering function which filters out all signals except those that meet particular filter criteria. Typical filter criteria are: (1) pulse height of greater than a predetermined threshold; (2) pulse width between 14–18 autocorrelation buffer samples; (3) pulse shape that is a local peak between and in close proximity to two local minimums; and (4) a pulse shape that has substantial vertical symmetry. Multiple candidate signals frequently result from this autocorrelation process. A digital signal processor stores the candidate signals in a candidate signal array wherein each candidate is represented by its peak-to-trough pulse height and its frequency in beats per minute. An arbitration function then selects the most likely EKG signal from among the candidates. A running average of the last few heart rates selected from previous candidate arrays is kept as an indicator of the user's current heart rate. That running average is used as an aid in making the arbitration selection among the candidates in the array of the most likely EKG signal.

Another example of the type of an EKG pulse rate monitoring machine of the type described above is found in U.S. Pat. No. 5,243,993 which is also owned by Life Fitness. In this patent autocorrelation and signal indication apparatus are also used. The signal indication routines however scan the output of the autocorrelator for the presence of periodic signals using different search criteria such as peak and waveform detection to generate a candidate heart rate.

In the prior art, it is known to place the contacts for an EKG type pulse monitor on the handles of exercise equipment. For example, U.S. Pat. No. 4,319,581 teaches placing three electrical contacts for a pulse monitor on the handlegrips of a bicycle such that when the user is exercising, one hand makes contact with two of the contacts, and the other hand makes contact with the third contact.

U.S. Pat. No. 4,938,228 to Righter is an example of a wrist worn EKG type heart rate monitor that probably represents closer prior art to the claimed invention than the other art discussed herein or known to the applicant. This device is intended to be mounted remotely from the heart and not use any electrode gel to improve contact to the skin and to find the EKG signal despite the low signal to noise ratio which results when the electrodes are not chest mounted and do not use electrode gel to improve electrical contact to the skin and when the user is exercising. In the approach taught by this patent, the sensed signal is modified and the characteristics of a first portion of the signal are learned. A second portion of the signal is then matched with the learned characteristics to produce a matched signal. The heart rate is then calculated from the matched signal. The characteristics of the first portion of the matched signal are learned by correlating the first portion of the matched signal with a prestored biological data to produce a correlated signal. A parametric screen and adaptive threshold are used to examine the correlated signal to determine whether it represents a ORS complex. If a ORS complex is recognized (ORS is a term of art referring to the three peaks of an EKG signal), an interval judge examines the timing between recognitions of ORS complexes to see if these intervals are consistent with what the user's heart rate should be. The interval judge outputs a counter output which represents the average interval time. A momentum machine smooths and averages the rate information and outputs it to a display.

Righter also teaches a performance predictor to tell the user how good or bad the machine will work on that user based upon the signal quality determined by the firmware. Also, the center frequency in both the hardware and software filters is 12 Hertz with a bandwidth of 6 Hertz. The applicant believes this performance can be achieved only with a recursive filter with non-integer coefficients. In a digital filter, use of floating point coefficients (non-integers) slows down calculation time and may require a special digital signal processor chip to handle floating point calculations the microprocessor cannot handle thereby further complicating the circuitry and increasing the expense. Also, the Righter machine uses a non-linear threshold calculation equation which is more complex than is necessary to get the job done. Further, the Righter template match operation is based upon autocorrelation with multiplications and additions rather than simpler and faster logical operations. The Righter machine uses two microcontrollers, one for digital signal processor (DSP) operations and one for implementing the user interface. This is more complicated than it needs to be if simpler filters were used.

Other examples of prior art pulse monitors are: U.S. Pat. Nos. 3,212,496 to Preston entitled "Molecular Physiological Monitoring System"; 4,038,976 to Hardy et al. entitled "Pulse Indicator"; 3,949,388 to Fuller entitled "Physiological Sensor and Transmitter" and 3,218,638 to Honig entitled "Wireless Passive Biological Telemetry System".

The class of products described above are generally used by health conscious people while working out. Because of the drawbacks of the two approaches described above, there has arisen a need for a reliable pulse monitor that is small and can be worn on the wrist or attached to exercise equipment and requires no electrode gel or moisture or chest strap and which can accurately find the EKG signal despite low signal to noise ratio.

DISCLOSURE OF THE INVENTION

The teachings of the invention contemplate of class of EKG based heart rate monitors which may be in wrist watch form or in a form for use on exercise machines and outdoor bikes or with chest straps in ambulatory, telemetric situations such as neonatal care or with hospitalized heart patients. The apparatus of the preferred embodiment of the invention comprise at least three electrodes which pick up EKG and EMG signals from the subject. These electrodes are coupled to an analog differential amplifier that cancels out common mode noise and amplifies the differential signals. The preferred gain level for the differential amplifier is from 5-10.

The output of the differential amplifier is, in the preferred embodiment at least, passed through an analog bandpass filter having a passband from 5-40 Hertz so as to suppress high frequency noise and 60/50 cycle hum picked up from the power lines. In the preferred embodiment, the passband filter is comprised of two separate hardware filters: a low pass filter with a first order rolloff and a corner frequency between 25-40 Hertz; and a high pass filter with a second order rolloff with a corner frequency of from 5-15 Hertz. The order of these two filters in terms of which filter filters the signals from the differential amplifier first, is not important. A separate hardware amplifier coupled to the output of the passband filter provides gain to the output signal from the hardware filter. The passband filter may also be active filter with its own gain in some embodiments, but such active filters can have oscillation problems where the gain is set too high. However, with that caveat, active filters are still preferred because the rolloff characteristics can be more precisely controlled and made steeper than passive components thereby providing more selectivity.

After filtering to remove some low and high frequency components, an analog amplifier having a gain preferably from 100-1000 is used to boost the signal level prior to conversion to digital format. The gain selected depends upon the gain selected for the differential amplifier and the gain of the active filters comprising the bandpass filter.

The output of this amplifier is fed to an analog-to-digital converter having a sample rate of 180 Hertz or some other multiple of 60 Hertz in the preferred embodiment.

Next, the signal is subjected to digital signal processing steps to filter out noise components above and below the EKG frequency band, emphasize the EKG signals against the noise and isolate the EKG based pulse rate.

BRIEF DESCRIPTION OF THE DRAWINGS

FIG. 13 represents the mathematical expression which completely specifies the digital signal processing which implements the recursive low pass filter step of block 90 in FIG. 7 with a notch at 60 Hertz.

FIG. 14 represents the mathematical expression which completely specifies the digital signal processing which implements the recursive bandpass filter step of block 90 in FIG. 7 with a notch at 60 Hertz.

FIG. 15 represents the mathematical expression which completely specifies the digital signal processing which implements the differentiation step 96 in Figure 11.

FIG. 16 represents the mathematical expression which completely specifies the digital signal processing which implements the moving average step 100 in FIG. 11.

FIG. 26 is a flow chart of an alternative embodiment for the process of FIG. 24(A) to provide for an automatic gain control function which changes the scaling or gain factors in the running average calculation.

FIG. 27 is a drawing of an alternative form for the contacts on the handlebars of an outdoor bike or exercise bike etc.

FIG. 28 is a cross-section of a detachable button contact and its mating receiver.

FIG. 29 ia a side view of a snap-ring mount for the detachable button type contact.

FIG. 30A is a top view of outdoor bike rider gloves with built in buttons electrodes that snap into receiver electrodes mounted on a bike handlebars.

FIG. 30B is a top view of outdoor bike rider gloves with built in buttons electrodes that snap into receiver electrodes mounted on a bike handlebars.

BEST MODE OF CARRYING OUT THE INVENTION

Figure 1:
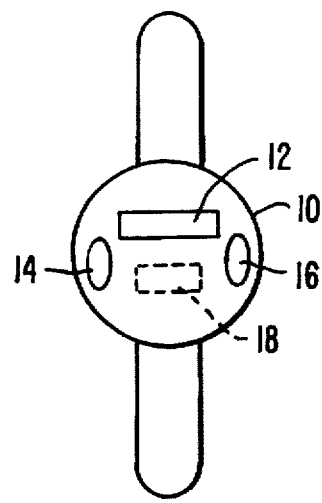
FIG. 1 shows a typical application in a digital wrist watch for the EKG type heart rate monitor according to the teachings of the invention.

Referring to FIG. 1, there is shown a typical application in a digital wrist watch for the EKG type heart rate monitor according to the teachings of the invention. The digital watch 10 includes a display such as LCD display 12 which is used to display the time, and when the pulse monitor mode is selected, displays the user's heart rate. In some embodiments, a separate display can be used to show the pulse rate with the time simultaneously displayed in display 12. The digital watch embodiment uses a three contact approach to help eliminate noise. Two electrical contacts 14 and 16 are placed on the front of the watch for the user to place his or her fingers on when the pulse mode is entered. A third electrical contact is located on the back side of the watch and is indicated in phantom at 18. The three contacts are connected to a differential amplifier inside the watch so that common mode noise is suppressed. The circuitry and software described below is incorporated into the watch 10 so that the unit is stand alone.

Figure 2:
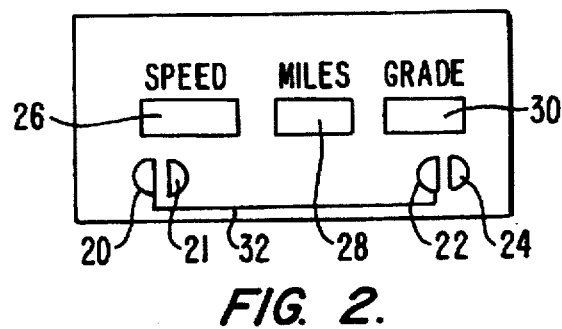
FIG. 2 is an illustration of a typical application of the invention on a treadmill, rowing machine etc.

Another application for the invention is symbolized by FIG. 2. This figure represents the control panel of a treadmill, exercise bike or stairmaster, and has four electrical contacts 20, 21, 22 and 24 on the front panel thereof along with a display 26 for speed, a display 28 for miles traversed and a display 30 for grade as appropriate for the particular machine into which the invention is incorporated. Contact 20 and 22 are connected together by a conductor 32 so as to make three total electrical contacts. In an alternative embodiment, the electrodes may be placed on handlebars or gripping rails normally clung to by the user during exercise as opposed to locating the electrodes on the control panel. To use this embodiment, the user places his or her fingers or palms on the two pairs of contacts while exercising and the user's heart rate is counted. Typically, the heart rate counting circuitry of the invention will automatically leave a sleep mode or power down mode (in battery operated embodiments) and enter a pulse counting mode whenever a user places a portion of his or her body into contact with the contacts. Either a proximity switch or some circuitry such as a comparator to measure analog voltage drop between the contacts and ground or some other reference will be used to sense when heart rate monitoring is desired. In machines such as treadmills or any AC powered machine which is constantly coupled to power, there is no need for sleep or power down mode, and heart rate counting mode can be continuously active.

Figure 3:
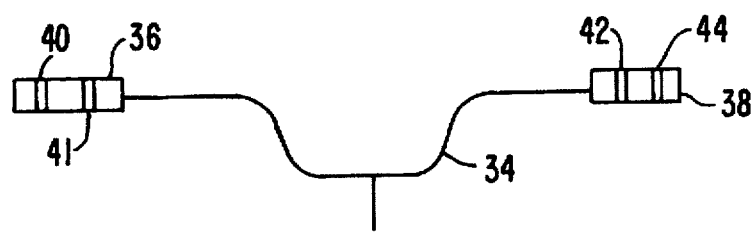
FIG. 3 is an illustration of a typical application of the invention on a stationary bicycle or an actual outdoor bicycle.

Another application for the invention is symbolized in FIG. 3 which depicts the handlebars 34 of an outdoor bike or an exercise bike with two grips 36 and 38 which are grasped by the user. Each grip has at least one electrical contact in the form of a conductive band or metal contact either on the front or back of the handle. In the embodiment shown in FIG. 3, two electrical contacts 40 and 41 are shown on handle 36, and two electrical contacts 42 and 44 are shown on handle 38. To use this embodiment, the user simply grips the handles. Heart rate mode is continuously active if the bike is continuously connected to power or is entered automatically from power down mode if a real bicycle or a bike not connected to power is used as the exercise vehicle. In the preferred embodiment, the handlebars have two electrodes on each side, the electrodes running circumferentially around the grip.

In some embodiments, an on/off switch controlling the heart rate mode is used. In automatic modes, the microprocessor (not shown) automatically times out and shuts down the pulse counting mode after either a predetermined time of no contact between the electrical contacts and the user or after a predetermined time of continuous pulse counting. In the latter case, a pushbutton switch may be provided to allow the user to force the machine to enter the pulse counting mode on demand. In another embodiment, the machine may cycle between a predetermined interval of pulse counting, an interval of showing the time and another interval showing calories burned etc.

Figure 4:
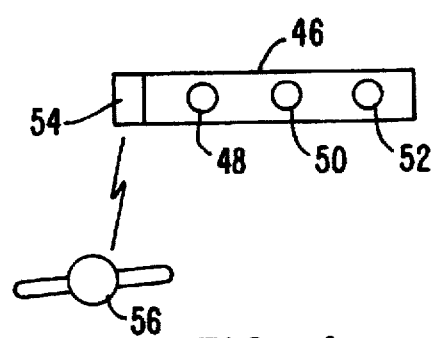
FIG. 4 is an illustration of a typical application of the invention on a telemetric chest band embodiment.

FIG. 4 represents another class of embodiments which use chest straps such as chest strap 46. The strap uses three electrical contacts 48, 50 and 52 which contact the chest of the user when the strap is worn. In one embodiment, the electrical signals sensed by these contacts are coupled to a transmitter 54. The transmitter will do the signal processing described below to detect each heart beat and generate a pulse for each heart beat. This pulse will be modulated onto an RF carrier and transmitted to a wrist display unit 56. Typically, the wrist display unit will have enough intelligence to account for missed beats in the form of an arbitrator which typically will check the interval between subsequent heart beats as compared to the interval between heart beats before the missed beat to determine if the heart rate has substantially changed. The results will be displayed. Also, if an extra beat is received unexpectedly during a refractory period between beats of the previously received string of beats, the wrist unit will have enough intelligence to ignore the extra beat as an artifact. Arbitration criteria may be used in some embodiments in eliminating extra beats such as a rule that the heart rate cannot change by more than 12.5% between adjacent beats. If an extra pulse occurs at a time which cause this maximum limit of heart rate change to be exceed, the pulse will be ignored. In alternative embodiments, the processing done by the wrist display unit 56 described above can be relocated to the chest strap unit and only data encoding the pulse rate will be transmitted to the wrist display unit. For medical applications, the technology described herein can be used with extra circuitry and software to sound an alarm if the pulse rate gets too low, too high or exhibits irregularity such as missed beats or extra beats.

The embodiments symbolized by FIG. 4 include telemetric chest strap monitors for athletes, telemetric neonatal monitors and telemetric ambulatory heart rate monitors.

Figure 5:
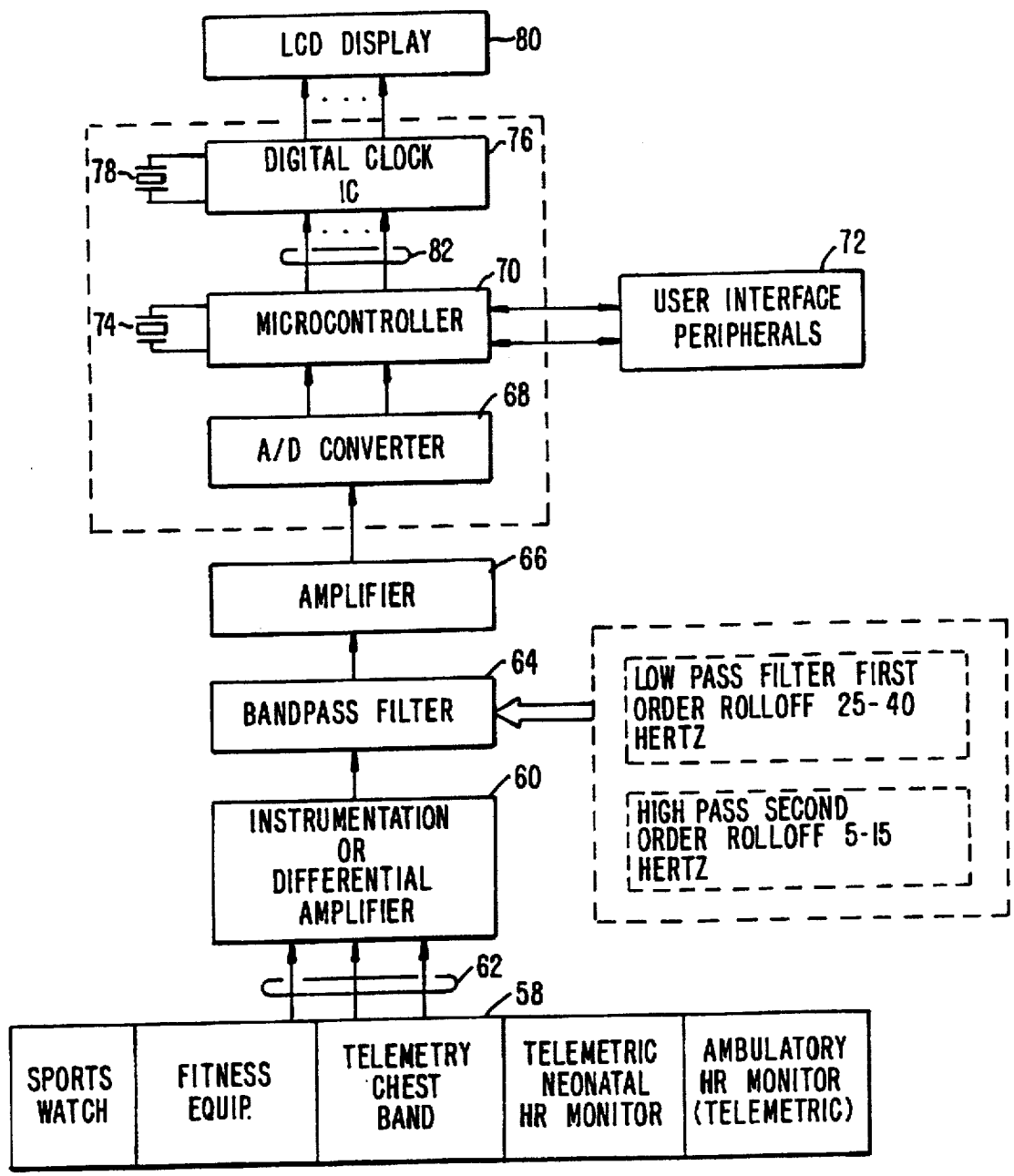
FIG. 5 is a block diagram of the preferred embodiment of the electronics of the invention.
Figure 6A:
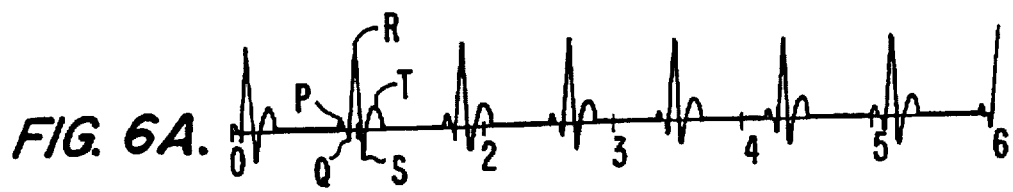
FIGS. 6(A)–6(a) are an illustration of some of the waveforms involved in illustrating some of the issues dealt with by the teachings of the invention.
Figure 6B:
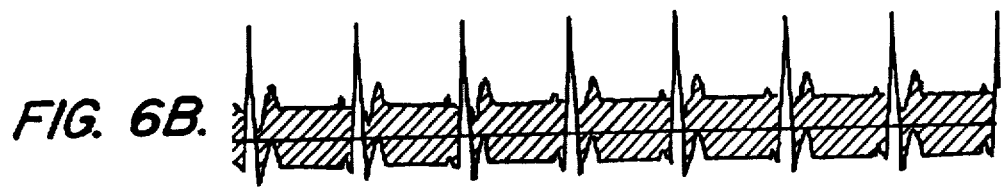
Figure 6C:
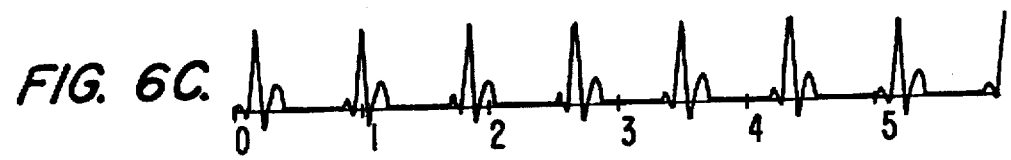
Figure 6D:
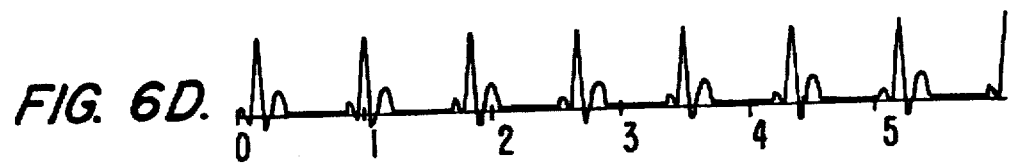
Figure 6E:
Figure 6F:
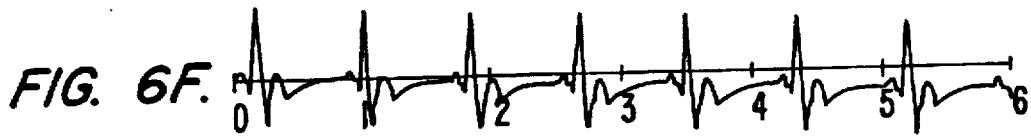
Figure 6G:
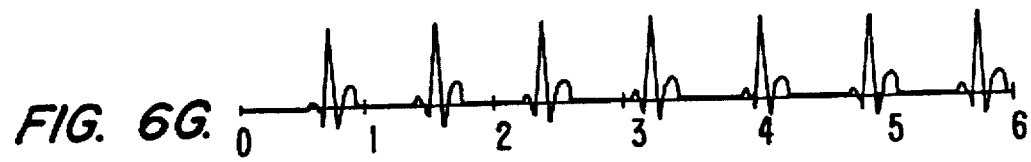

Referring to FIG. 5, there is shown a block diagram of the preferred embodiment for circuitry to implement the teachings of the invention. Block 58 represents the electrical contacts of any of the embodiments discussed above. Block 60 is a differential amplifier or instrumentation amplifier that is coupled via bus 62 to the contacts. The differential amplifier amplifies the analog signals on the three conductors of bus 62. The common input on bus 62 is coupled to analog ground and the two remaining conductors are coupled to the plus and minus inputs of the differential amplifier. The differential amplifier serves to provide gain and to simultaneously eliminate common mode noise in the signal such 60/50 Hertz hum etc. The gain of the differential amplifier is set at a relatively low figure of 5–10 to prevent saturation of the operational amplifiers therein by the low frequencies that are still in the analog signal.

Next, the output of the amplifier is filtered by an active analog bandpass filter 64. Active filters using RC components in operational amplifier circuits are used to implement the bandpass filter. The passband of this filter is centered on some frequency between 5 and 20 Hertz, preferably 10–15 Hertz, and has a passband of approximately 5–40 Hertz. The purpose of this bandpass filter is to remove high frequencies from the analog signal to prevent aliasing. The low frequency corner of the passband also eliminates DC components and any low frequency drift of the baseline caused by respiration muscle contractions or other muscle contractions such as typically occur when the user is exercising. The gain of the bandpass filter is preferably set at 1.5 at the center frequency, but that gain figure is not critical. A passive bandpass filter could be used, but generally is not preferred since it requires too many components and the rolloff is not sharp enough. In the preferred embodiment, the passband filter is comprised of two separate hardware filters: a low pass filter with a first order rolloff and a corner frequency between 25–40 Hertz; and a high pass filter with a second order rolloff with a corner frequency of from 5–15 Hertz. The order in which these two filters filter the incoming signal from the differential amplifier is not important. The reason these two filters have different order rolloffs is to allow the differentiator to emphasize the high frequency components in the signal in a manner described below. In other words, the steeper rolloff on the low frequency corner provides better selectivity, while the less steep rolloff on the high frequency corner allows more high frequency component to reach the differentiator such that the differentiator will generate bigger slope numbers because of the sharp peaks in the signal represented by the data reaching the differentiator because of the higher content of high frequency components in the analog signals reaching the analog-to-digital converter. These sharper corners cause the differentiation operation in the digital signal processing portions of the circuit to be described below to generate higher peaks. These higher peaks are filtered out by the moving average function, but in the process, the average rises thereby causing the EKG signals to stand out better against the background noise.

Next, the analog signal is amplified in amplifier 66 which has a gain of 100–1000 so that the overall gain is about 1000–10,000.

Next, the analog output of the amplifier 66 is applied to the input of an analog-to-digital converter (hereafter AD converter) 68, which, in the preferred embodiment is integrated onto the microcontroller integrated circuit. The analog signal is converted to 8-bit digital samples at a sampling rate of 180 Hertz, or some other multiple of 60 Hertz preferably. Other sampling rates can also be used so long as the high frequency components of the real signal from the electrodes have been filtered out prior to the real signal reaching the analog-to-digital converter. If these high frequency components have not been filtered out, alias signals will appear in the EKG frequency range resulting from beating of the sampling rate with the high frequency components. This is why use of an analog bandpass filter in front of the analog-to-digital converter is preferred. Different numbers of bits in each sample could be used as well as a higher or lower sampling rate, but 180 Hertz is preferred to make the digital filtering easier since the 180 Hertz sampling rate is a multiple of the 60 Hertz frequency of a common source of noise. Further, the coefficients for the digital signal processing stages described below are set for a sample rate of 180 samples per second, so if other sample rates are used, the coefficients must be optimized again. In some embodiments, the AD converter is part of a microcontroller integrated circuit 70. The AD converter should be able to operate on a 3 volt supply or some supply voltage easily achievable with batteries and, for size considerations in some embodiments, preferably has a serial format output data stream if the AD converter is not integrated onboard the microcontroller.

The digital data stream from the AD converter is input to the microcontroller 70 for further signal processing to be described below. The microcontroller is preferably a 4-bit or 8-bit machine such as a Samsung KS57C2408 or Hitachi H8/3812 or equivalent. These microcontrollers have on-board analog-to-digital converter, dual clocks, LCD drive and buzzer drives. There is no need for an on-board DSP or a separate DSP since the digital filter coefficients are integers which substantially simplifies and speeds up processing in the software filtering modules. The microcontroller is also coupled to a number of user interface peripherals represented by block 72. The user interface peripherals include LCD displays, mode control switches, buzzer(s), sensors for monitoring track/wheel speed or as part of an automatic feedback loop which will cause more drag on the wheel/track when the heart rate drops below a target range, and output ports to which different resistors may be connected to change the gain of the operational amplifiers, output signals to implement automatic load variation in embodiments where the drag on the belt/wheel is automatically varied in accordance with the user's heart rate, such as circuitry to change the gears on a mountain bike to a lower gear or higher gear automatically based upon the user's heart rate, and alarm units to give users audible alarms when something is not working or needs adjustment. The microcontroller has its own clock 74 which can be shut down along with the microcontroller in power down mode so that a digital clock chip which has its own clock is not disabled during power down mode of the microprocessor.

In some embodiments, a separate digital clock integrated circuit 76 with its own clock 78 serves to keep track of the time/date etc. and control the display thereof. In alternative embodiments, the digital clock chip can be any digital clock chip where display 80 displays only time and date so long as the clock chip has an interface to the microcontroller 70 to receive heart rate data. However, in the preferred embodiment, digital clock IC 76 is incorporated into the microcontroller and receives for display data encoding the heart rate reading, calories burned, speed, distance covered, exercise time etc. via the conductors of bus 82 for display on LCD display 80.

There follows a discussion of the digital signal processing implemented by the firmware which controls operations of the microcontroller 70. However, to better understand the approach used, the characteristics of a typical EKG signal and an EKG signal with noise will first be discussed. Referring to FIG. 6, there is shown a number of waveforms on time lines (A) through (G). Time line (A) shows a typical EKG signal, which is sometimes referred to as a QRS complex. An EKG signal is comprised of a first small positive peak designated as P on time line (A), followed by a negative peak designated Q. After the negative Q peak, a very large positive peak immediately follows which is designated as R on time line (A). The R peak is immediately followed by a negative S peak which is immediately followed by a smaller positive T peak. The slope of the R peak is symmetrical on both sides and has a unique characteristic value.

Time line (B) shows a EKG signal superimposed with 60 Hertz line interference. Time line (C) shows the result of passing the signal of time line (B) through a second order Butterworth lowpass filter. The signal on time line (C) still exhibits some 60 Hertz noise. Time line (E) represents and EKG signal superimposed upon a low frequency noise sources such as respiration EMG or exercise EMG signals. Time line (F) shows the result of passing the signal of time line (B) through a second order Butterworth high pass filter showing distortion of the signal from the action of the filter. Time line (D) shows the signal resulting from passing the noisy signal of time line (B) through an integer coefficient low pass filter such as is used in the invention. Time line (G) shows the signal resulting from passing the signal of time line (E) through an integer coefficient high pass filter such as is used in the invention. Both low and high pass integer coefficient filters are used in the invention to eliminate both 60 Hertz noise and low frequency noise.

Figure 7:
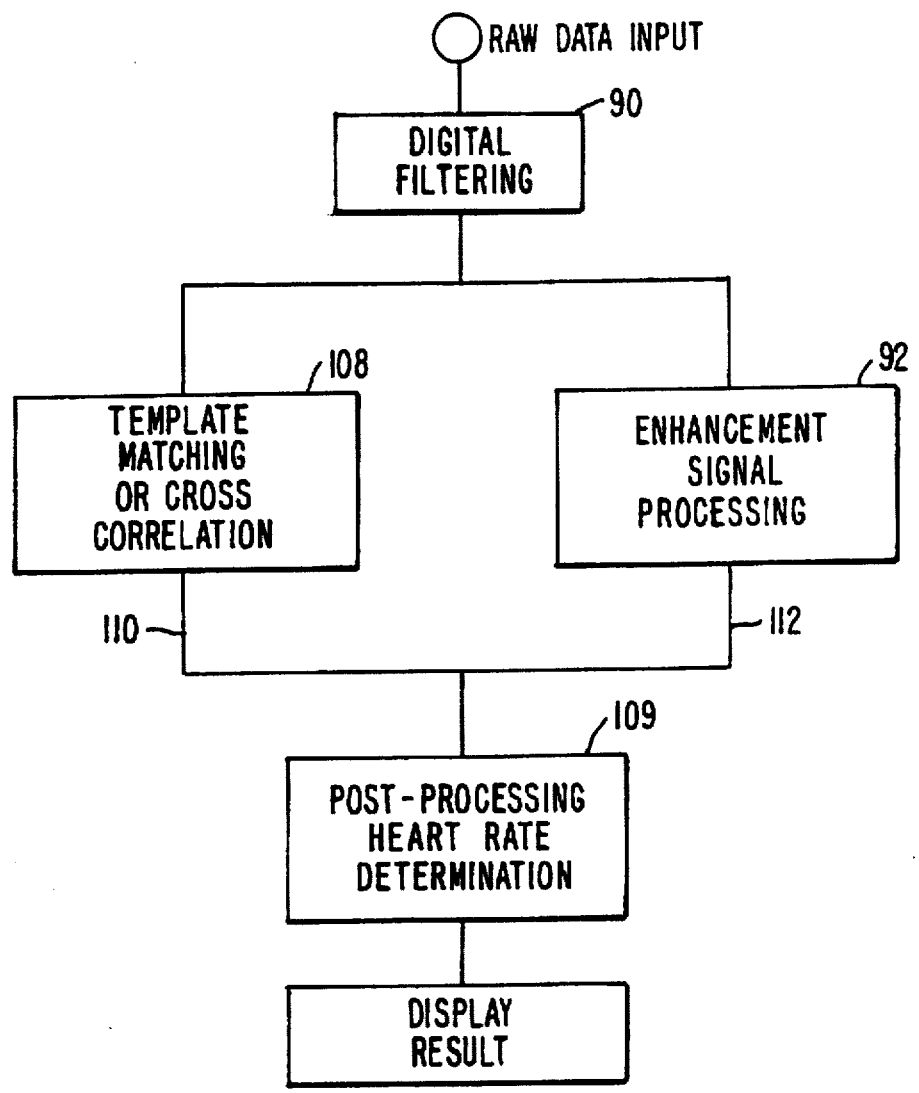
FIG. 7 is an overview flow chart of the software architecture according to the teachings of the invention.

Referring to FIG. 7, there is shown a flow diagram of the main processing carried out by microcontroller 70 on the digital samples received from the AD converter 68. The digital filtering which results in the signals on time lines (D) and (G) in FIG. 6 is represented by the digital filtering block 90. The function of this block is to remove high and low frequency noise from the digital samples.

The digital filtering steps represented by block 90 comprises, in the preferred embodiment, a first step of low pass filtering the incoming digital data with a low pass filter having a notch at 60 Hertz and then passing the resulting filtered data through a bandpass filter which amplifies the signals in a frequency range from 10–40 Hertz and has a notch at 60 Hertz. The reason a low pass filtering step is used prior to passing the data through the low pass filter is to remove remaining high frequency components in the incoming data prior to passing the signals through the bandpass filter for amplification and further filtering.

Figure 8:
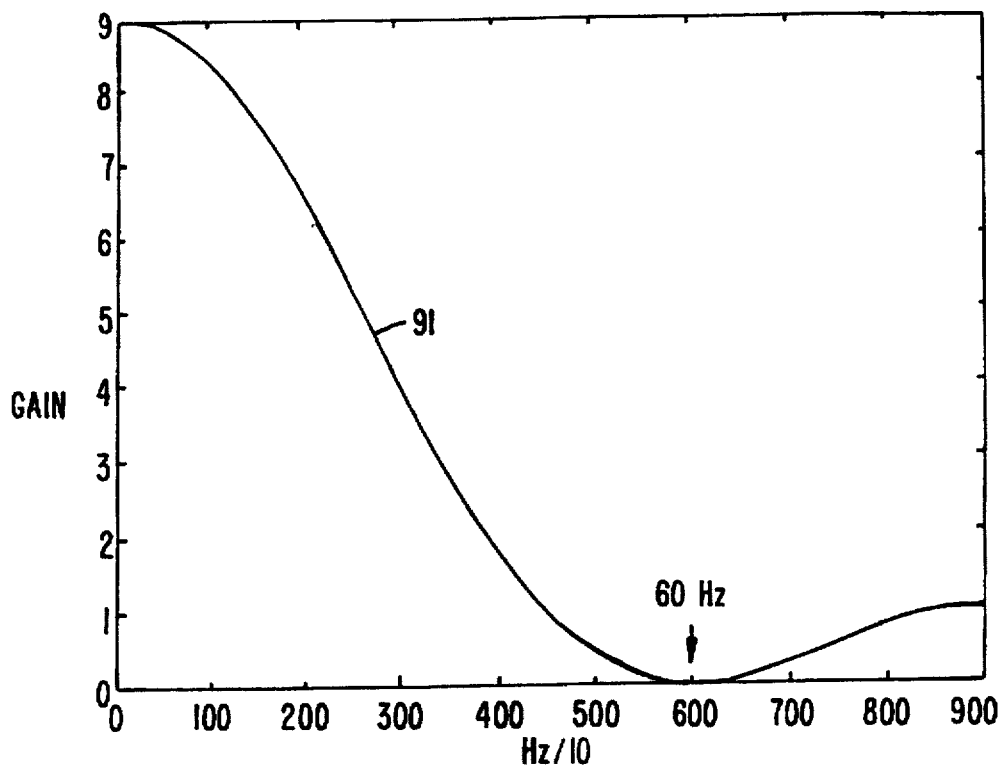
FIG. 8 is a graph of the filter response of a digital low pass filter used in the preferred embodiment of the invention.

FIG. 8 represents the frequency response of the preferred embodiment for the digital low pass filter implemented by the preferred embodiment of the digital filtering step 90 in FIG. 7. This digital filtering is achieved by implementing a recursive filter having integer coefficients to simplify and speed up the calculations required to implement the filter. However, any digital or analog filter that implements a frequency response roughly equivalent to the frequency response of FIG. 8 will suffice for purposes of practicing the invention, e.g., non-recursive, recursive with different integer coefficients or floating point coefficients, separate DSP etc., analog or any combination of the above. In fact, the low pass filtering step can be eliminated altogether in some embodiments. The purpose of the low pass digital filter is to remove 60 Hertz noise and to enhance signal to noise ratio.

Figure 9:
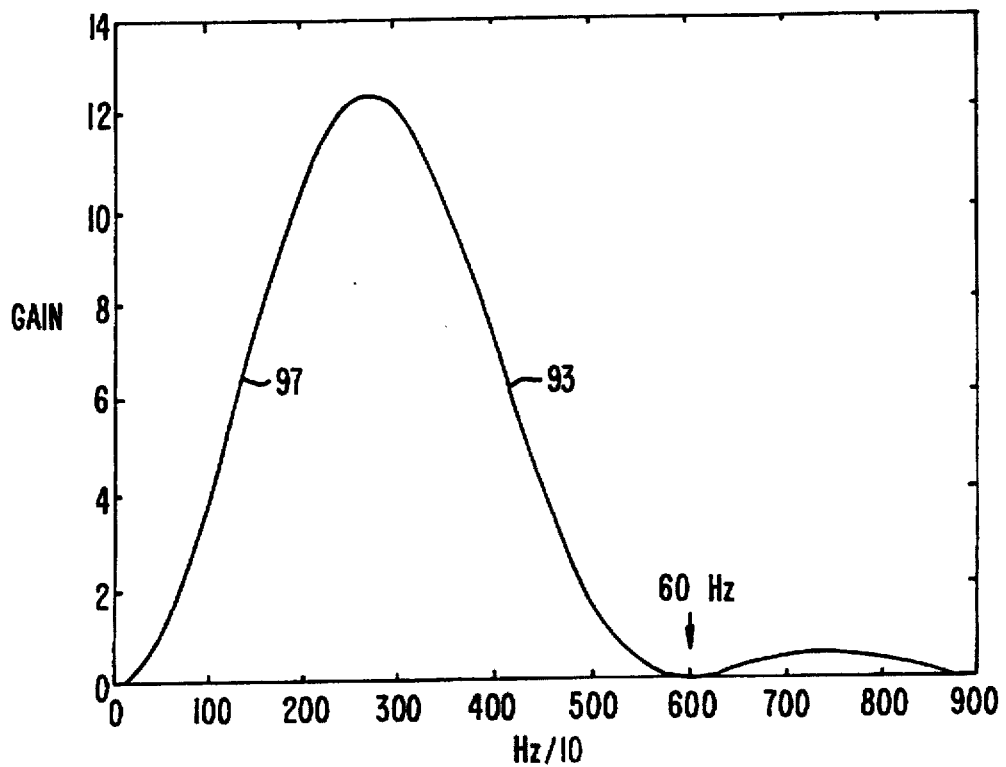
FIG. 9 is a graph of the filter response of a digital bandpass filter used in the preferred embodiment of the invention.

FIG. 9 represents the frequency response of the preferred embodiment of the bandpass filter implemented as the second stage of digital filtering represented by block 90 in the preferred embodiment. This digital filtering frequency response is achieved by implementing a recursive filter having integer coefficients to simplify and speed up the calculations required to implement the filter. However, any digital filter that implements a frequency response roughly equivalent to the frequency response of FIG. 9 will suffice for purposes of practicing the invention, e.g., non-recursive, recursive with different integer coefficients or floating point coefficients, separate DSP etc. or any combination of the above. The bandpass filter function could also be done using an analog filter. One purpose of the bandpass filter is to reduce low and high frequency EMG signals caused by exercise, respiration and muscle tremor in addition to further reducing 60 Hertz hum noise. Some of the above mentioned EMG signals lie outside the passband and are therefore attenuated. EMG and other noise signals in the passband are removed by a learning, adaptive threshold detect operation and further uses rules of reason implemented in the software to arbitrate whether pulses which exceed the adaptive threshold are true heart beats or are artifacts or noise.

Figure 10:
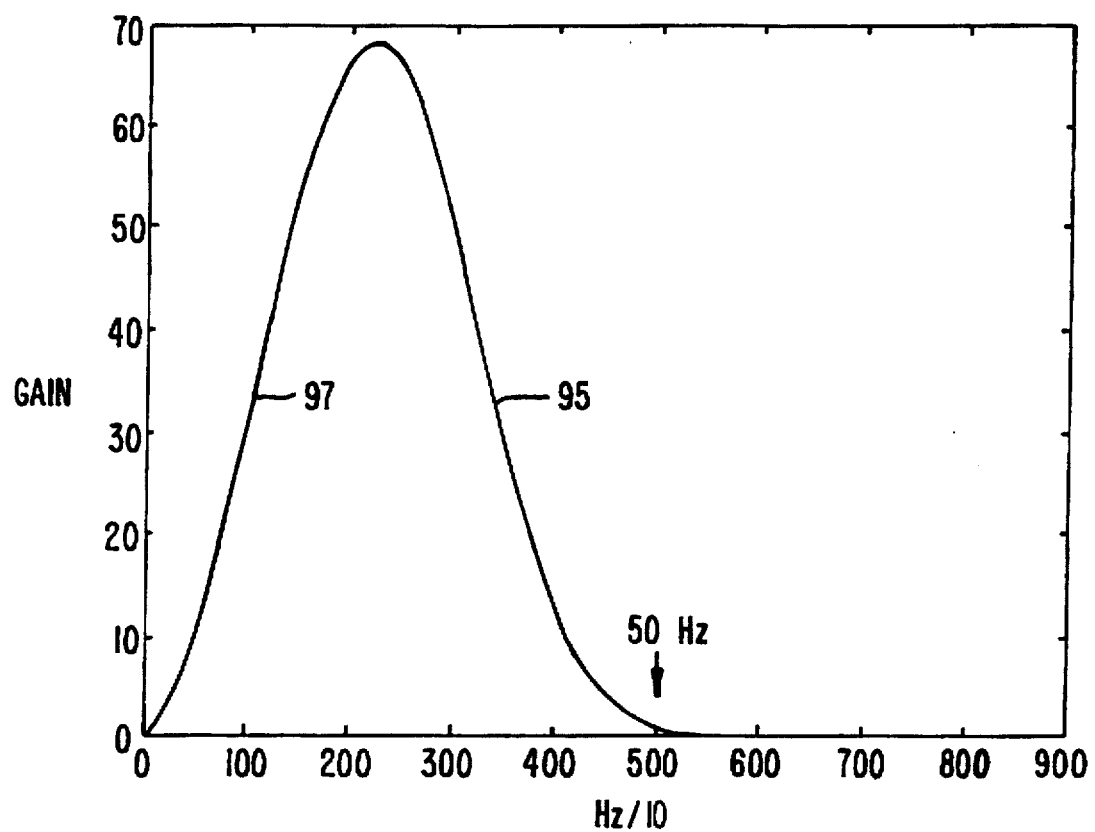
FIG. 10 is a graph of the total filter response resulting from combining the effects of the digital low pass filter and the digital bandpass filter.

The low pass filtering step can be eliminated in some alternative embodiments since the bandpass filter also removes the high frequencies. However, the low pass filter is preferred because if it is not present, there is less effective filtering out of 50 Hertz noise which is only an issue if the invention is to be used in any European or other country where 50 Hertz power is used. In those markets, the presence of the low pass filter improves performance for the following reason. Note that the rolloff 91 of the low pass filter at the high frequency corner is 2nd order. Note also that the rolloff 93 of the bandpass filter transfer function at the high frequency corner is also 2nd order. The combined filter response/transfer function implemented by block 90 is shown in FIG. 10. The combination of the 2nd order rolloff 91 of the low pass filter and the 2nd order rolloff 93 of the bandpass filter results in a 4th order rolloff 95 in the overall filter response which has virtually no gain at the 50 Hertz frequency thereby effectively removing 50 Hertz noise. Note also that although the bandpass filter has a 2nd order rolloff 97 at the low frequency corner, the low pass filter has no rolloff at the low frequency. Therefore, the resulting rolloff at the low frequency corner of the overall frequency response is only 2nd order. This is too much rolloff on the low frequency corner would destroy some of the sought after data.

Returning to the consideration of the overall digital signal processing represented by FIG. 7, after digital filtering is performed, two different processes are performed to find the EKG signal in the filtered data. In the preferred embodiment, only the enhancement signal processing represented by block 92 is performed. In the best embodiment, template matching or cross-correlation is also used to provide alternative results which can be cross-checked against the results of the enhancement signal processing.

Figure 11:
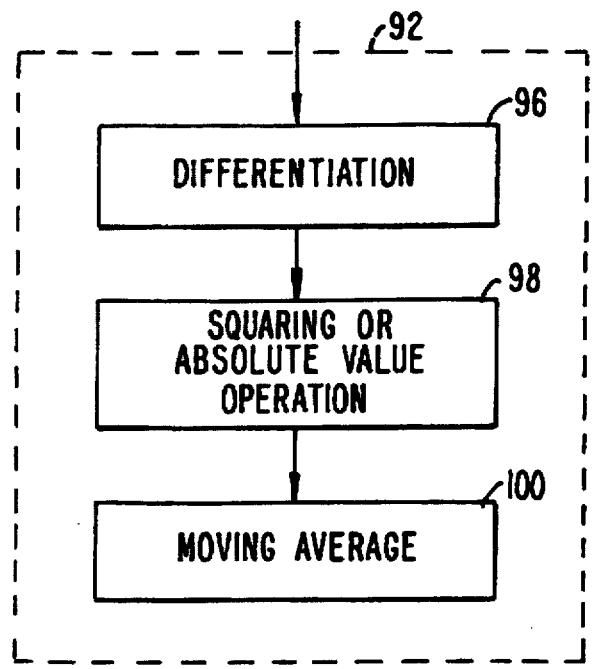
FIG. 11 is a more detailed flow diagram of the enhancement signal processing of the right branch in FIG. 7.
Figure 12A:
FIG. 12 is an illustration of the waveforms that illustrate the operation of the processing of FIG. 11.
Figure 12B:
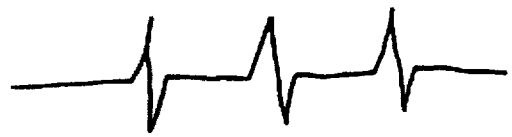
Figure 12C:
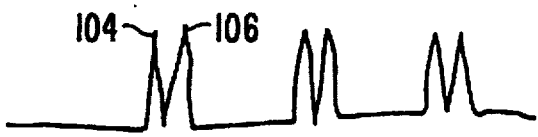
Figure 12D:
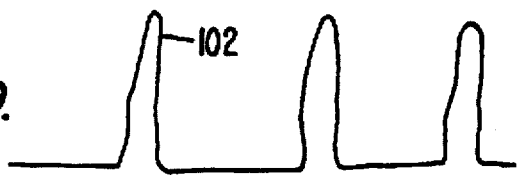

Referring to FIG. 11, there is shown a flow chart of the basic operations that are performed in the enhancement signal processing block 92. The first step is differentiation, represented by block 96. The reason this differentiation operation is performed is because the filtering process removed some of the information content of the EKG signal, but there is still a fairly high spectral content of high frequency Fourier components of the EKG signal caused by the Q, R and S peaks which is within the passband of both the analog and the digital filters. To enhance this component, the differentiation process is performed on the array of sample data to find the slopes of all peaks in the data. The incoming filtered data has a signal waveform which can look like the waveform at time line A in FIG. 12. The differentiation process receives this waveform and outputs a waveform that looks like the signal on time line B in FIG. 12.

The slopes of the two sides of each peak in the signal on time line A are successively positive and then negative. Because a moving average (an integration step) is to be calculated to smooth out the output of the enhancement signal processing output and to improve the signal to noise ratio, negative peaks are undesirable because they tend to cancel positive peaks and make the signal to noise ratio worse. To get rid of the negative peaks and possibly improve the signal to noise ratio, in the preferred embodiment, a squaring operation represented by block 98 is performed. The squaring operation outputs a waveform like that shown on time line C of FIG. 12. Note that all negative peaks are converted to positive peaks.

Because squaring requires multiplication, and because multiplication is slow and consumes too much computing resource, the preferred embodiment is to substitute a look up table containing the squares of all values likely to be found in the input signal to avoid the processing necessary in multiplication. This is much faster than actually performing the multiplication. In an alternative embodiment, an "absolute value" step can be performed for block 98. This absolute value operation receives both positive and negative peaks and outputs a signal which is all positive peaks, each representing the absolute value of the magnitude of a corresponding positive or negative peak. Squaring is preferring since this has the effect of multiplying the size of the peaks in the signal thereby enhancing the signal to noise ratio.

Finally, a moving average is computed as represented by block 100. The purpose of calculating this moving average is to smooth out any sharp spike-like peaks in the output of the squaring operation or absolute value step. The moving average computation is like an integration which calculates the area under each peak in the output from the squaring or absolute value step. The moving average step also increases the signal to noise ratio by taking each pair of peaks in the signal output by block 98 and summing the area under each curve. This enhances the amplitude of the resulting single peak which results from each pair of adjacent peaks in the signal on time line C. For example, peak 102 results in the output of the moving average step from the integration or filtering of the pair of peaks 104 and 106 that arrived from the squaring step. The moving average is calculated by taking a predetermined number of sequential samples and adding their values and then dividing the sum by the number of samples so added. The individual samples in each moving average can be weighted in some embodiments. This process is carried out continuously for each contiguous group of samples.

FIG. 13 represents the mathematical expression which completely specifies the digital signal processing which implements the recursive low pass filter step of block 90 in FIG. 7 with a notch at 60 Hertz. The Y terms represent previous outputs such that $Y_{n-1}$ represents the most recent previous output while $Y_{n-2}$ represents the second most recent previous output. The X terms represent recent data, except that the result of a previous stage's calculation, e.g., $Y_n$ in FIG. 13 becomes raw data point $X_n$ for the next stage, e.g., $X_n$ in FIG. 14 is actually the result $Y_n$ from the calculation process represented by FIG. 13. For example $X_n$ represents the most recent data while $X_{n-4}$ represent the fourth most recent data and so on. Note how the coefficients of the recursive filter specification represented by FIG. 13 are all integers thereby greatly speeding up and simplifying the calculation. There are many different combination of coefficients which can result in acceptable filter transfer functions. There may even be other filter specifications with more points or different subscripts which result in acceptable filter responses. FIG. 13 only represents one acceptable example, and any alternative that results in a similar range of frequencies in the passband as shown in FIG. 8, and relatively similar gain levels will be acceptable. The factor $\frac{1}{8}$ in the equation of FIG. 13 is a normalization factor based upon the gain of the filter.

FIG. 14 represents the mathematical expression which completely specifies the digital signal processing which implements the recursive bandpass filter step of block 90 in FIG. 7 with a notch at 60 Hertz. The same can be said about other possible alternatives to the filter specification of FIG. 14 as was said about FIG. 13. The factor $\frac{1}{12}$ in the equation of FIG. 14 is a normalization factor based upon the gain of the filter.

FIG. 15 represents the mathematical expression which completely specifies the digital signal processing which implements the differentiation step 96 in FIG. 11. Many other combinations of weighting coefficients, numbers of sample points and possibly even different subscripts exist. For example, the denominator 4 in FIG. 15 is chosen so as to make the result of the differentiation process larger such that the input data to the squaring process is larger. This results in greater dynamic range. However, other denominator factors exist which can be used without departing from the invention defined in the claims. Any such combination that result in a filter characteristic that has the same relative range of frequencies within the first major loop of the transfer function where most of the useful work gets done will be acceptable to practice the invention. For example, different numbers of sample points with a different divisor will also work to practice the invention.

FIG. 16 represents the mathematical expression which completely specifies the digital signal processing which implements the moving average step 100 in FIG. 11. The moving average function has the effect of amplifying the low frequency components. The number of points selected for the "window" over which the moving average is calculated is important in that it defines where the first notch is in the transfer function which has the characteristic of defining how high the amplitude is of the resulting moving average peak. Eight points were selected in the preferred embodiment to enhance the signal-to-noise ratio by raising the amplitude of the peak that results from each peak pair in the signal from the squaring or absolute value operation of block 98 in FIG. 11. Other values for signal-to-noise ratio would also work, but perhaps not as well. For example, 16 points would smooth the output more, but the amplitude of the peak is lower. A number of points fewer than 8 may result in a sharper peak with more adjacent noise thereby resulting in lower signal to noise ratio. The $\frac{1}{64}$ factor in front of the summation is a scaling factor which can be used as a digital gain control factor. In some embodiments, the adaptive learning process will be used to affect this digital gain control factor based upon characteristics found in the sample data.

Referring again to FIG. 7, in an alternative embodiment, a second type of signal processing of the digital data after digital filtering is carried out as a cross check against the results of the enhancement signal processing or as an alternative thereto. The alternative or additional processing is symbolized by block 108 and involves template matching in the preferred embodiment or cross-correlation where adequate processing power is available to do the multiplications involved in the cross-correlation calculation. Template matched filtering is preferred since it is much faster and involves no multiplication since simple exclusive-or logic operations are used. The template matched filtering is basically a crude but fast way of performing rudimentary cross-correlation to determine the degree of likeness between two waveforms. The way it is done is as follows.

Figure 17A:
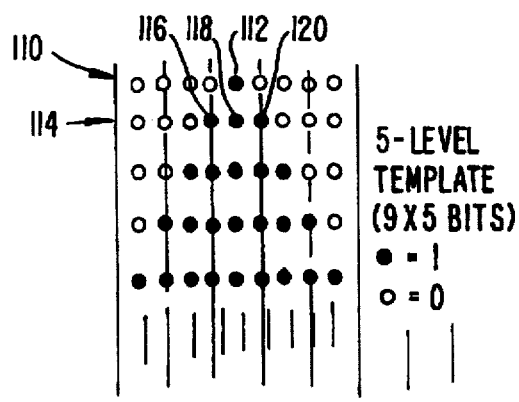
FIGS. 17(A) and 17(B) represent the logic template used in the cross-correlation process by logic operations and shows how input signals are sliced at 4 or 5 different levels to generate data to be compared against the logic template.
Figure 17B:
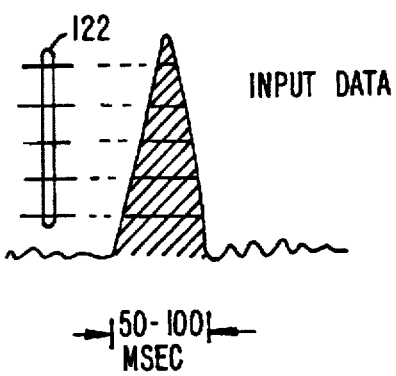

Referring to FIG. 17, comprised of FIGS. 17(A) and 17(B) there is shown the manner in which input data is compared to a template in memory to determine the degree of similarity in an input waveform to a reference waveform. Specifically, FIG. 17(A) shows a 5×9 bit array in memory that contains a pattern of logic 1 arranged in a shape which emulates the shape of the R pulse in a QRS EKG waveform. The array is comprised of five rows, each of which has nine bits therein. Row 1, shown at 110 contains only a single logic 1 in the middle position of the row shown at 112 representing the peak of the R waveform and all other bit positions store logic 0s. Row 2, shown at 114, contains three logic 1s at 116, 118 and 120 and all other bit positions or logic 0s. Each successively higher numbered row in the five row array contains a greater number of bits simulating the triangular or Christmas tree shaped R pulse. Nine bits were chosen for the size of the array rows since typical R peaks in QRS waveforms span about 50 to 100 milliseconds and nine data points result every 50 milliseconds at the sampling rate of 180 Hertz used in the preferred embodiment. If a faster sampling rate is used, more data points are used at every level of the template which results in more accuracy.

FIG. 17(B) shows a typical peak represented by the digital data that is output from the digital filtering step. In one embodiment, the input pulse is "sliced" horizontally at five different levels from the peak to the base of the signal, as symbolized by the horizontal lines shown at 122. The process of slicing the input signals involves determining the peak amplitude of each incoming peak and dividing that amplitude by the number of levels of slicing to be performed. In the preferred embodiment, only 4 slices are used and the array of FIG. 17(A) is 4×9 since a 5 layer slice and a 5×9 matrix does not offer any noticeable advantage over a 4 layer slice and a 4×9 matrix. Once the peak amplitude has been divided by the number of slices to be used, the slices are taken across the peak separated by the degree of amplitude derived from this process of determining how far apart each slice must be to fit the required number of slices into the size of the peak. The template matching process is not amplitude sensitive. It is the shape of each peak compared to the shape of the template which determines the amplitude of the peak in the digital data representing the signal at the output of the "cross-correlation" template matching process.

However many slices are used, each slice is converted to a "byte" of 9 bits, each bit representing a timeslot. The timeslots of this byte have logic 1s in timeslots representing points (corresponding to sample points) that are inside the "envelope" of the peak, i.e., the cross-hatched area under the peak, and all timeslots representing points in time outside the envelope have logic 0s therein, i.e., timeslots representing locations outside the cross-hatched area. The process of converting each slice to a byte of data is performed on the fly as each new batch of data arrives by a suitably programmed microprocessor. As the phrase "on the fly" is used herein, a 16 sample window is used as the raw data, and as each new sample arrives, the window is shifted by one sample.

Each byte of real data generated in this fashion is matched by an exclusive-or matching operation carried out either in serial or parallel format by a suitably programmed microprocessor to compare each bit position of the template to each corresponding bit position of the real data. A number of logic 1s is output for each slice that corresponds to the number of "hits", i.e., corresponding bit positions in the template and the real data that are both logic 1s.

The above described template matching process is done "on-the-fly" with a fixed time delay. That is, it is performed continuously on the input data as each new batch of 16 sample points arrives. The fixed time delay represents the latency time while 16 new sample points of real data arrive.

Figure 18:
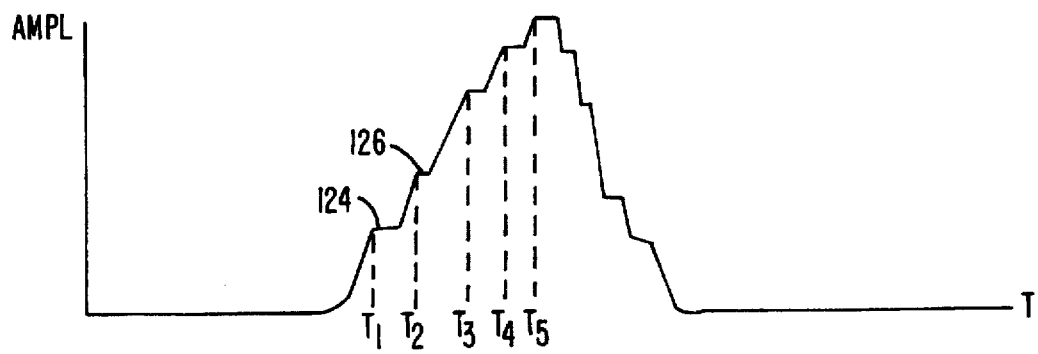
FIG. 18 is a drawing illustrating how digital data resulting from the cross-correlation by logic template comparison symbolized by FIG. 17 defines an output pulse when the input pulse has the same approximate shape as the logic template.

The number of logic 1s output for each slice is converted to an amplitude to generate an output signal like that shown in FIG. 18. To generate the output waveform of FIG. 18, the number of hit on the baseline slice, i.e., the lowest slice is converted to the amplitude 124 at time $T_1$ and output to the post processing module 109 in FIG. 7 as digital data representing the amplitude at 124 of a result waveform. Then the number of hits on the next slice up is converted to digital data representing the amplitude at 126 of the result waveform at time T2 and output to the post processing module 109 in FIG. 7. This process is continued for all slices, and the process is repeated for each successive batch of new data samples on a continuous basis in embodiments using the template matching form of signal enhancement.

The waveform of FIG. 18 represents a significant number of hits meaning that the shape of the template matches well to the shape of the peak in the sample data representing the actual signal sensed during a particular time interval. This means that there is a high probability that the resulting waveform of FIG. 18 will be judged in the post processing module 107 to represent an actual heartbeat and not an artifact.

The processes of block 108 and 92 in FIG. 7 have the effect of removing artifacts and noise and enhancing the peaks in the incoming data which are likely to be actual QRS EKG waveforms. In the process of block 92, the differentiation step of block 96 in FIG. 11 tends to remove or suppress EMG peaks and enhance EKG peaks because the EKG peaks have steeper slopes and sharper tips than typical EMG waveforms. This results in larger numbers being output from the differentiator for EKG signals that have been differentiated than for EMG signals. This fact translates to higher peaks in both the positive and negative amplitudes in the signals on time line B of FIG. 12 representing the differentiator results from differentiating EKG QRS waveforms than result from differentiation of typical EMG pulses. This further suppresses EMG noise and enhances the signal to noise ratio.

The template matching or cross-correlation process of block 108 removes artifacts by virtue of suppressing peaks that do not have the shape of the template. The template is designed to simulate closely the shape of the QRS waveform in a typical EKG waveform. In some embodiments, the shape of the template will be adjusted "on-the-fly" after actual EKG signals are isolated for this particular user so as to more closely match the shape of the QRS waveform of this particular user. Suppressing of EMG waveforms and other noise and artifacts occurs because these spurious signals do not have the same shape as the template and therefore result in lower correlation peaks in the output data of the template matching process.

Figure 19:
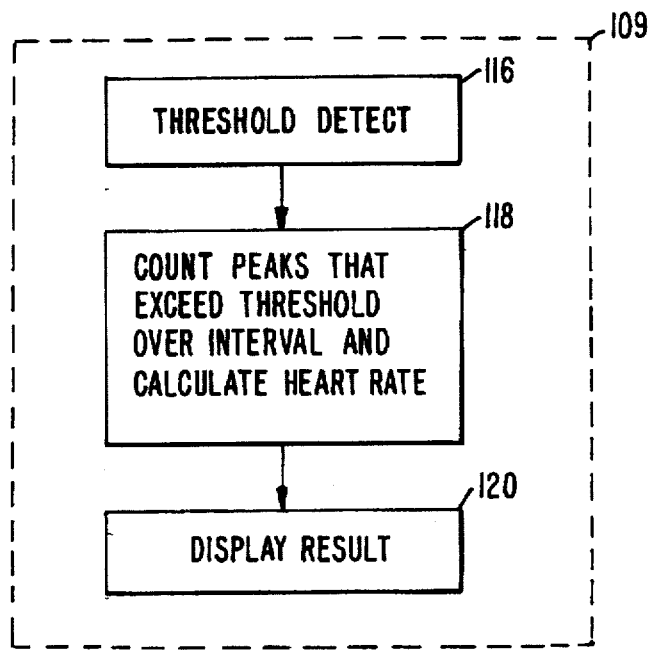
FIG. 19 is a flow chart of one alternative embodiment for the post-processing module 109 in FIG. 7.

After enhancement of the digital data and removal of as many artifacts as possible in the enhancement process, either by the process of block 92 or block 108 in FIG. 7, the resulting digital data is analyzed to determine the user's current heart rate. This is done by post-processing heart rate determination module 109 in FIG. 7. The process represented by block 109 could be any one of a large number of different types of discrimination or arbitration routines to decide which of the pulses in the filtered, enhanced data from either path 110 or path 112 in FIG. 7 represent actual heart beats and to calculate the heart rate therefrom. One possible embodiment for the process of block 109 is shown in FIG. 19. In this embodiment, a threshold detect process 116 is performed where a threshold amplitude level is compared to the amplitudes of all peaks in the incoming data. The threshold may be fixed or variable, and, if variable, it may be either adaptive or user programmable. The threshold level is selected such that only EKG pulses will usually have sufficient amplitude to exceed the threshold. If the threshold is adaptive, a learning process to determine the heart rate and then set up a window around the expected time of each EKG pulse can be employed to isolate EKG pulses from noise and learn their average amplitude. Once the average amplitude of EKG pulses is learned, the threshold is set at a level approximately 50% of the average amplitude or some other amplitude level which prevents most noise peaks from exceeding the threshold. If the threshold is user programmable, the user may vary the threshold until a heart rate is displayed which corresponds to a pulse count the user takes manually and then the threshold may be set permanently at that level or left variable such that it can be adjusted during each use.

Block 118 represents the process of counting peaks that exceed the threshold over some predetermined interval and calculating the heart rate from the count by dividing the count by the number of seconds in the interval and multiplying by 60 seconds/minute. In block 120, the calculated heart rate is displayed.

Figure 20:
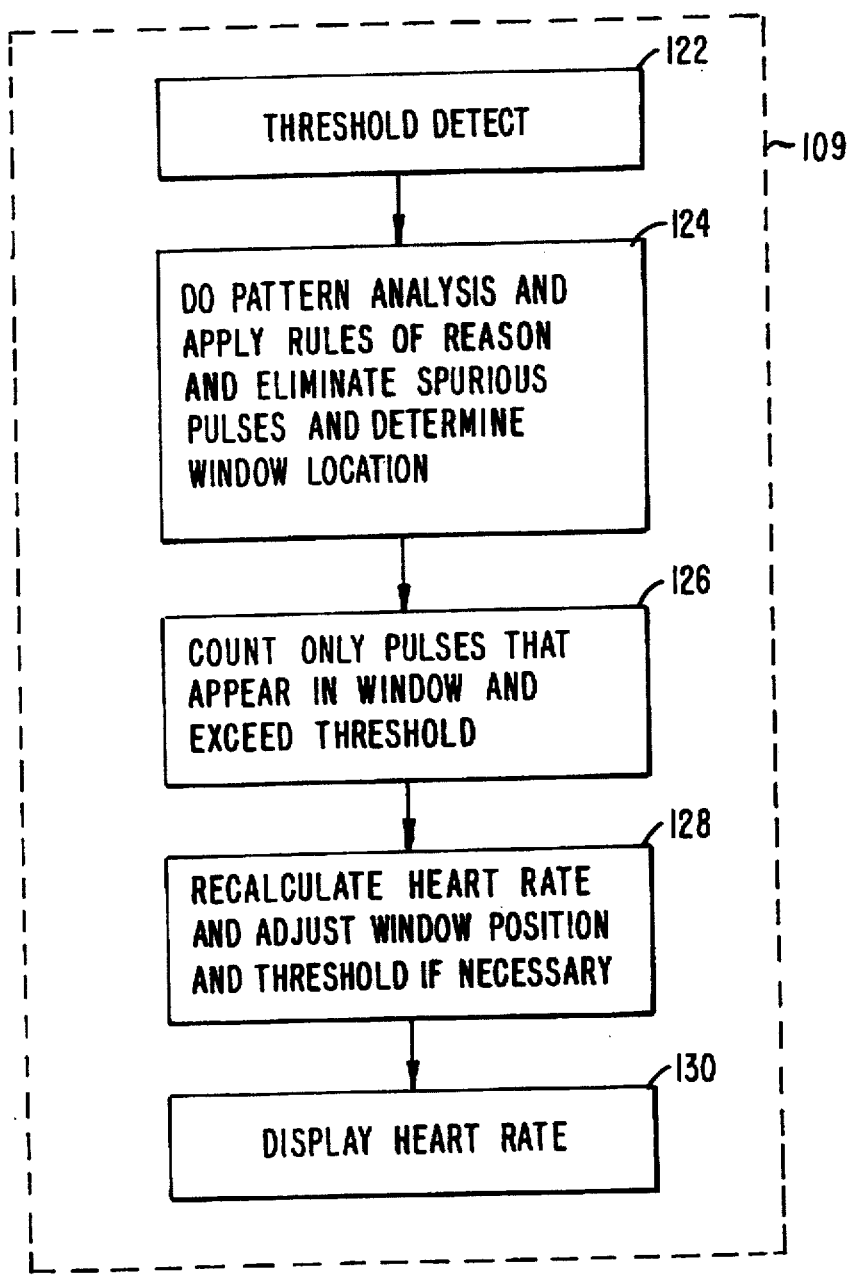
FIG. 20 is a flow chart of another alternative embodiment for the post-processing module 109 in FIG. 7.

FIG. 20 represents another alternative embodiment for the post-processing heart rate determination process represented by block 109. The process starts out with a process of comparing each incoming pulse to a threshold level established relative to the average EKG pulse amplitude so as to screen out many artifacts but low enough so as to not miss EKG pulses, as symbolized by block 122. The process of block 124 is performed next wherein the pulses which exceed the threshold are subjected to a pattern analysis wherein evidence of periodicity in the pattern of pulses which exceed the threshold is examined. Once a candidate period is found, a preliminary heart rate is calculated from this period and rules of reason are applied to the preliminary heart rate. The rules of reason can be based upon any known factors that are true of all human heart rates. For example, a human heart rate will always be between 30 and 220 beats per minute and will never change by more than 12.5% in the interval between adjacent beats. If the preliminary heart beat calculated from the pattern analysis fails any rule of reason test, the preliminary heart rate is rejected and a new pattern analysis on a new set of data is performed. After a preliminary heart rate is found which satisfies the rule of reason test, the timing of a window is calculated, said window timed to open during a predetermined interval during which each new EKG pulse is expected to occur. After the window is set up, spurious pulses between the times when the window is open are eliminated from the data.

Next, in step 126, pulses which exceed the threshold and occur during the window times are counted. Then, in step 128, the heart rate is calculated and the rule of reason tests are applied again to see if the new heart rate makes physical sense. If not, the new heart rate is rejected and the process starts over with a new pattern analysis. If the new heart rate is plausible, the position of the window is adjusted further and the threshold level may be adjusted if too many spurious pulses are being found and eliminated between times when the window is open. Finally, the new heart rate is displayed in step 130.

Figure 21:
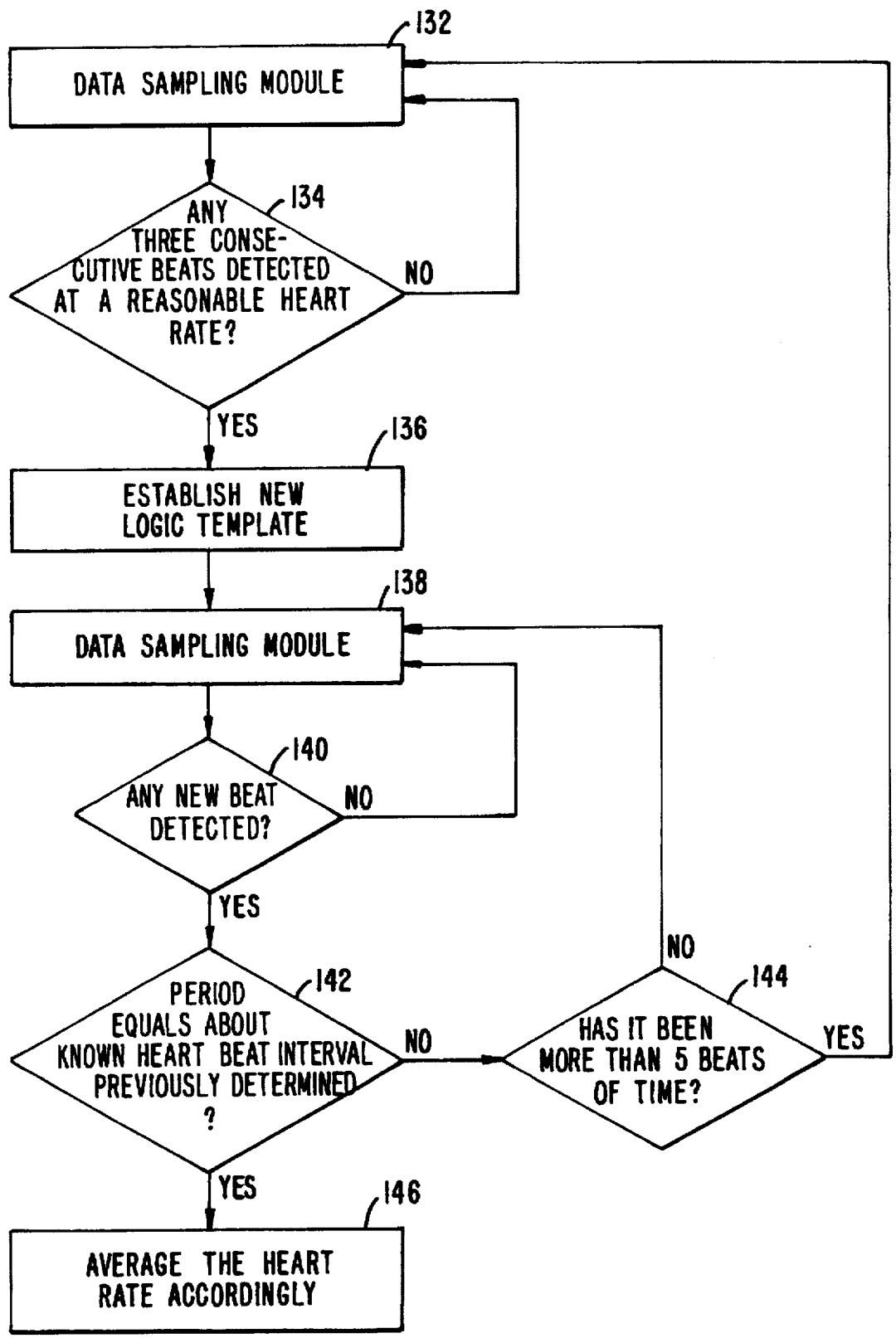
FIG. 21 is a flow chart of another alternative embodiment for the post-processing module 109 in FIG. 7.

Referring to FIG. 21, there is shown another alternative embodiment for the post-processing heart rate determination of block 109 in FIG. 7. Step 132 represents the process of sampling the data output by the data enhancement process (es) of blocks 92 and/or 108 of FIG. 7 and testing the pulses in the data using a threshold comparision. Test 134 determines whether any three consecutive pulses seem to be periodic and represent a reasonable heart rate within the physical limits from 30 to 220 beats per minute. If not, processing returns to block 132 to do more sampling of new data and threshold comparison. If three consecutive beats are found which seem to represent a reasonable heart rate, the process of block 136 is performed to set a new logic template for use in the logical operation cross correlation operation described with reference to FIGS. 17 and 18.

After the new template is established, the process of block 138 is performed to again sample the new enhanced digital sample data generated by the process(es) of blocks 108 and/or 92 using the new logic template. Next, the test of block 140 is performed to determine if any new beats that appear to be periodic are detected using the new logic template. If not, processing returns to step 138 to sample more new data for analysis by test 140. If a new series of periodic beats (or, in some embodiments, a single beat using the new template) was detected using the new template, a test 142 is performed to determine if the period of the new string of beats or the new beat relative to the last of the three consecutive beats previously detected is approximately equal to the interval previously determined. If not, the test 144 is performed to determine if an interval approximately 5 heartbeats long has passed. If not, processing returns to block 138 to resample the data generated with the new template. If 5 heartbeats have passed using the new template and no new beat has been detected, the template is deemed to be defective or input data is not valid caused by loose contacts etc., and processing returns to block 132 to start the learning process again. If test 142 determines that a new heart beat has been detected, the period of the new heart beat is averaged with the period of the previously determined heart beat, and displayed in block 146.

Figure 22:
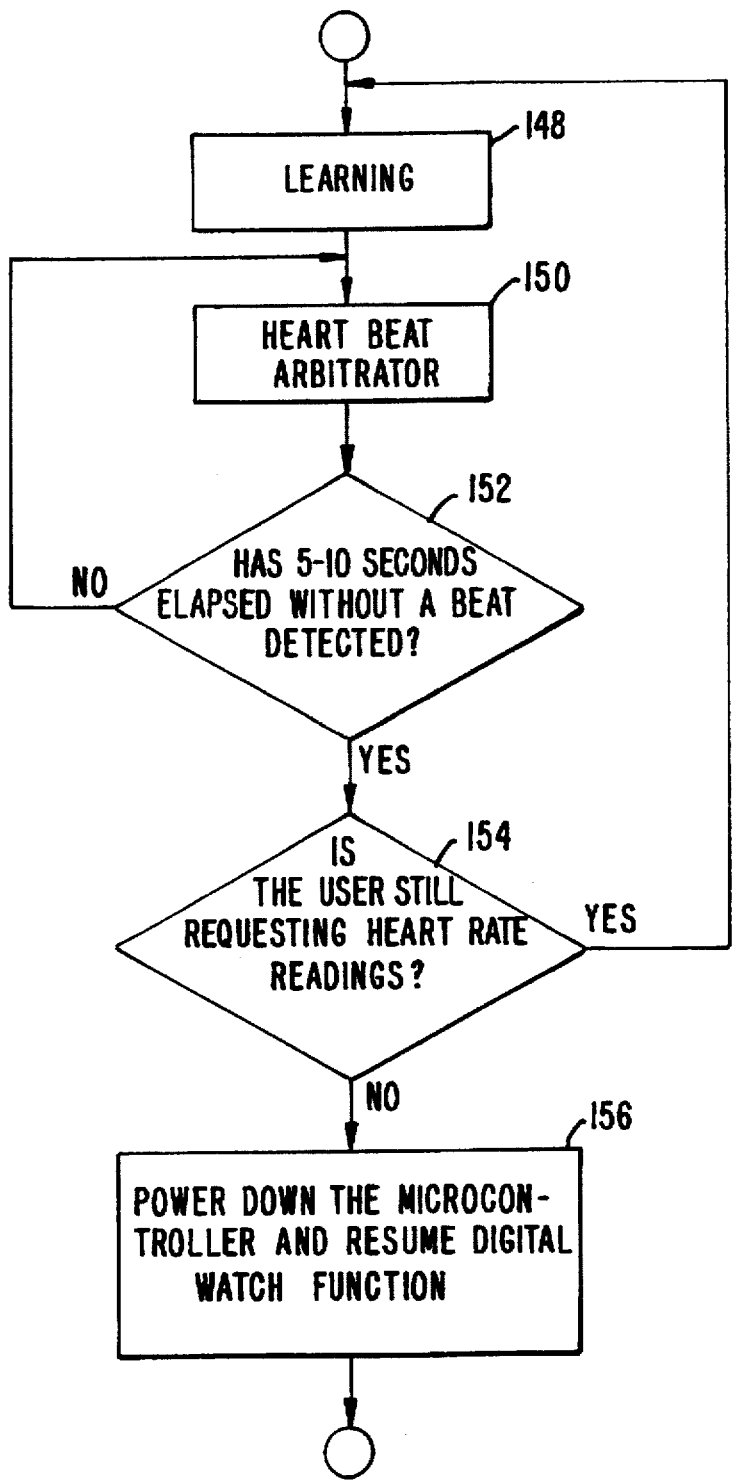
FIG. 22 is an overview flow chart of the processing of the post processing module 109 in FIG. 7.

Referring to FIG. 22, there is shown an overview of the preferred embodiment for the post-processing heart rate determination module represented by block 109 in FIG. 7. The process starts out by attempting to learn the characteristics of this particular user's EKG signal, as symbolized by block 148. The details of this process will be described in more detail below.

Next, after the characteristics of this user's EKG signal have been learned, the process of block 150 is performed to determine which pulses in the input stream of digital data represent actual EKG signals. The input data to the process of block 148 can come from either path 112 or path 110 in FIG. 7. In alternative embodiments, one path or the other may be used in accordance with which processing, i.e., block 92 or block 108 in FIG. 7, is providing better signal-to-noise ratios. Switching between paths in such an embodiment is controlled by a quality arbitrator process which is not shown herein but which can be any process which yields the best signal- to-noise ratio data. The details of the heart beat arbitrator will be described in more detail below.

Next, the test of block 152 is performed to determine if 5–10 seconds has elapsed without a beat having been detected. If not, processing vectors back to the process of block 150. If no beat has been detected in 5-10 seconds, the test 154 is performed to determine if the user is still requesting heart rate readings. Typically, the user requests heart rate readings by placing the unit in heart rate mode by pressing a button on the unit or by placing his body in contact with the sensors. If heart rate readings are still requested, processing vectors back to the learning process of block 148 to relearn the characteristics of this user's EKG waveform. If the user is no longer requesting heart rate readings, the process of block 156 is performed to power down the microcontroller and resume the digital watch function. This conserves battery power.

Figure 23A:
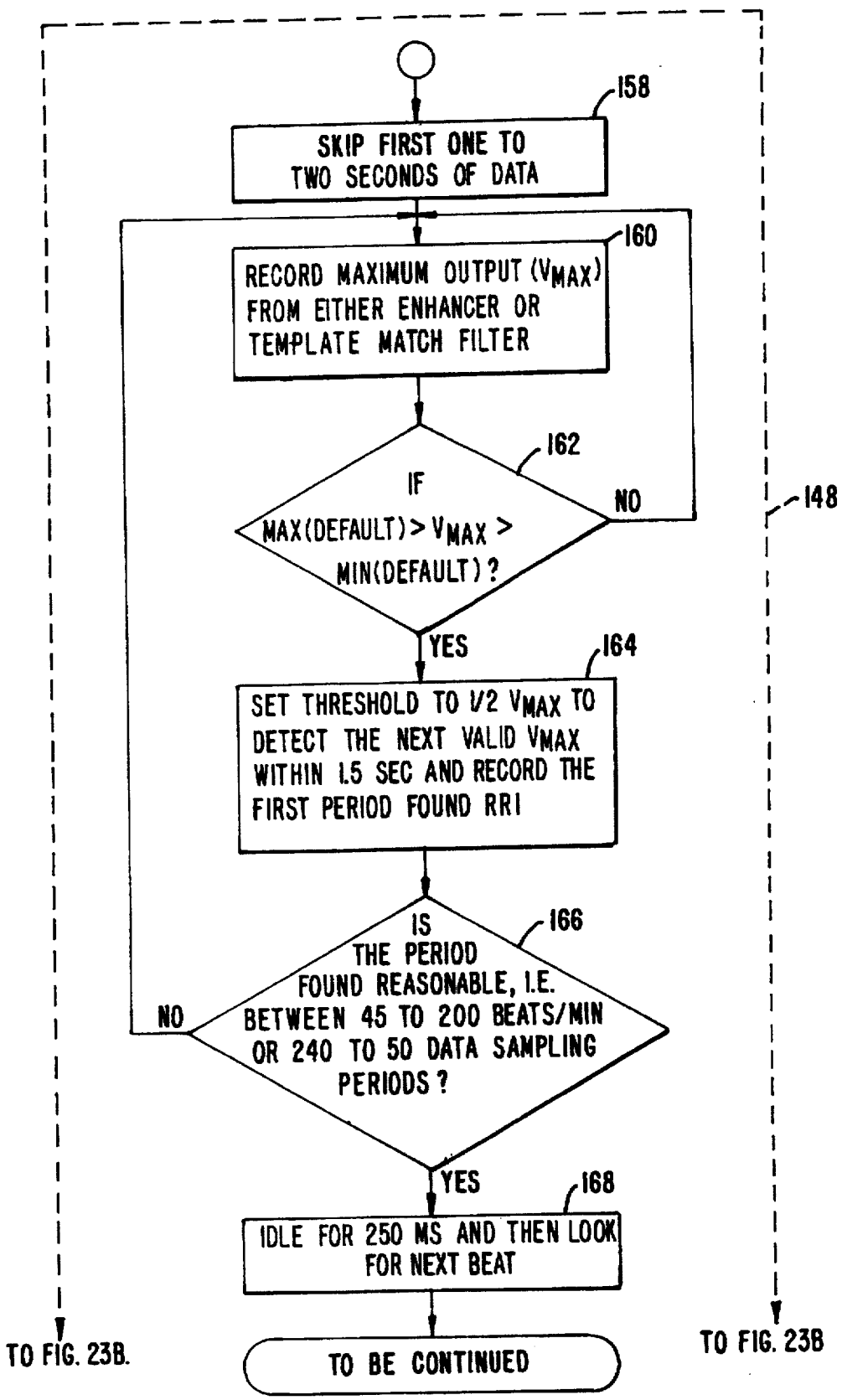
FIG. 23, comprised of FIGS. 23(A) and 23(B), is a detailed flow chart of the preferred embodiment for the learning process represented by block 148 of FIG. 22.
Figure 23B:
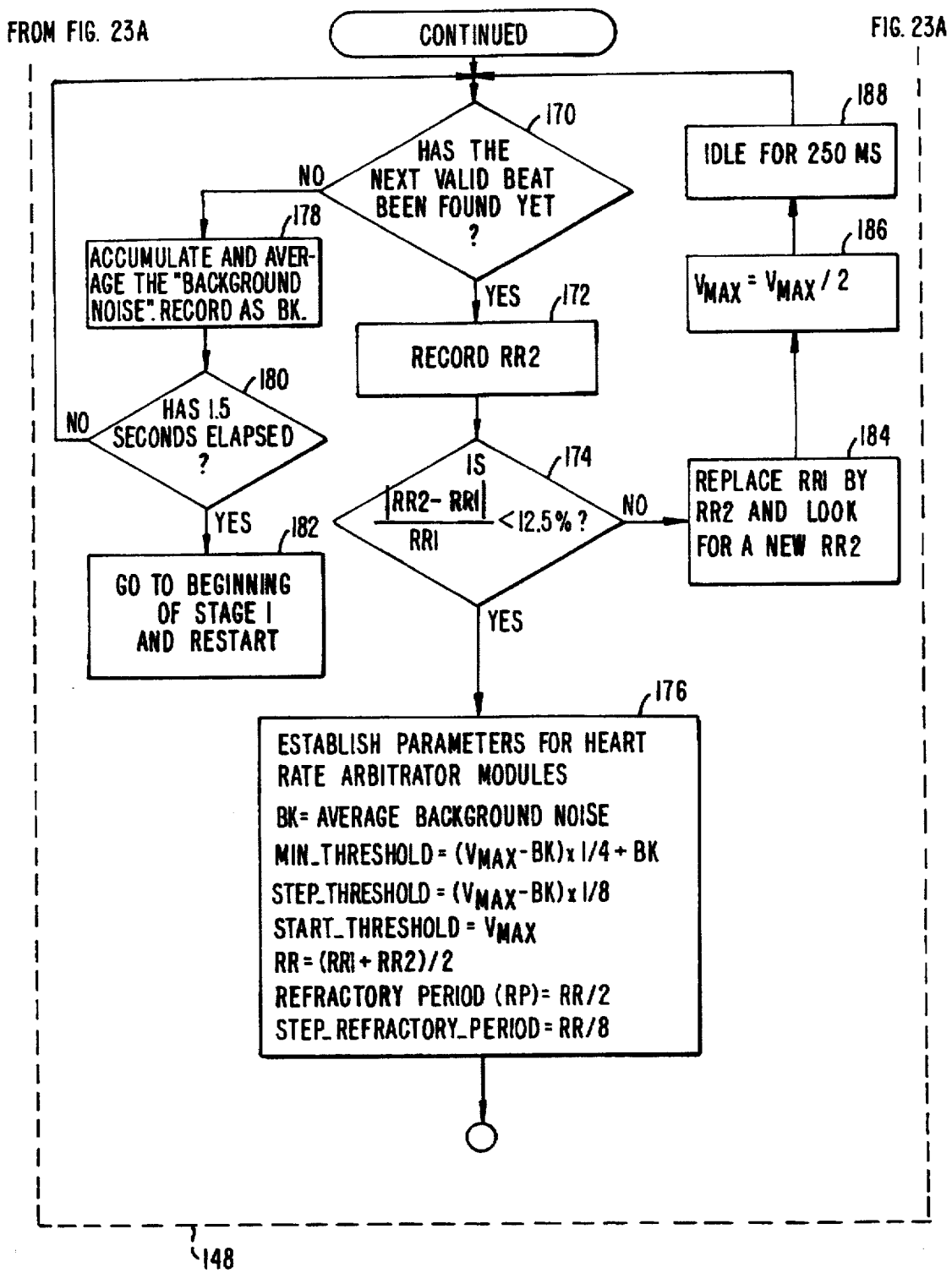

FIG. 23, comprised of FIGS. 23(A) and 23(B), there is a shown a detailed flow chart of the preferred embodiment of the learning process represented by block 148 in FIG. 22. Usually the incoming stream of data includes artifacts, typically resulting from EMG signals, loose contact between body and sensor that are much larger in amplitude than the desired EKG pulses despite the filtering and enhancement operations that have preceded the learning process. EMG signals often have the same approximate frequency as the EKG signal when a user is exercising thereby making the filtering process more difficult. Therefore, it is desirable to learn the characteristics of the desired EKG signals so as to be able to better distinguish between EKG signals and EMG signals and other artifacts. The first step in this process, represented by block 158 is to skip the first few seconds (1-2 second of data) of sample data as that data is deemed to be unreliable when the contact between body and electrodes is first made and impedance values may be varying substantially enough to invalidate the resulting sample data. Next, step 160 is performed to record the maximum output amplitude $V_{max}$ of any pulse in the data resulting from processing by either the enhancement signal processing block 92 in FIG. 7 or the template matching process of block 108 of FIG. 7.

Next, test 162 is performed to determine if $V_{max}$ is greater than a default variable MIN and less than a default variable MAX. If it is, the processing proceeds to step 164. If not processing returns to block 160 to start the learning process over again.

Step 164 sets the level of a discrimination threshold to ½ $V_{max}$ and then examines more incoming data using this discrimination threshold to find the next valid $V_{max}$ within 1.5 seconds of setting the new threshold. It will always be true that the next heart beat will occur within 1.5 seconds of the time the discrimination threshold is set. If a new heart beat is found within the next 1.5 seconds, the first heart rate period is recorded as variable RR1.

Next, test 166 is performed to determine if the first heart rate period recorded as RR1 is reasonable, i.e., between 45 and 200 beats per minute or between 240 to 50 sampling periods. If the variable RR1 is not between these limits, processing returns to block 160 to start the learning process all over again. If RR1 is found to be within reason, step 168 is performed to idle for 250 milliseconds before starting to examine the incoming data for the next EKG pulse. This 250 milliseconds represents a latency period during which the occurrence of another EKG pulse would be impossible.

After waiting the first latency period and then starting again to look for an EKG pulse, test 170 is performed to determine if a valid EKG signal has been found. If it has, the period between this new EKG pulse and the preceding EKG pulse is recorded as a variable RR2, as symbolized by block 172. Then, to make sure that the new heart rate does not violate a rule of reason that the new heart rate cannot differ from the old heart rate by more than 12.5% in adjacent heart beats, test 174 is performed. Test 174 determines if the absolute value of RR2 minus RR1, quantity divided by the value of RR1 is less than 12.5%. If it is, then it is determined that a valid heart rate has been found and the characteristics of the pulses in the input data which have been assumed to be EKG signals are, in fact, EKG signals an array of whose characteristics are to be recorded at the conclusion of the learning process. To accomplish this learning, block 176 is performed where the values of an array of different variable parameters are set for use by the heart rate arbitrator module represented by block 150 in FIG. 22. The variable parameters recorded in block 176 include: setting a variable BK equal to the average background noise; setting a variable Min_Threshold equal to $(V_{max}-BK) \times \frac{1}{4} + BK$; setting a variable Step_Threshold equal to $(V_{max}-BK) \times \frac{1}{8}$; setting a variable Start_Threshold equal to $V_{max}$; setting a variable RR equal to (RR1+RR2)/2; setting a refractory period variable RP equal to RR/2; and setting a variable Step_Refractory_Period equal to RR/8.

Returning to the consideration of test 170, if it is determined there that no new, valid EKG pulse has been found after the latency period, the step 178 is performed to accumulate and average the "background noise" and record the average as the variable BK. Then test 180 is performed to determine if 1.5 seconds has elapsed. If not, processing returns to test 170 and it is determined if a new, valid heart beat has been found yet. If 1.5 seconds has elapsed, and no new, valid EKG signal has been detected, processing is vectored to block 182 where processing is vectored back to block 160 to restart the learning process again.

Returning to the consideration of test 174, if it is determined that the change between RR1 and RR2 exceeded 12.5%, step 184 is performed where the value of RR1 is overwritten with the value of RR2 and the process of examining the incoming data for a new EKG signal to establish a new value for RR2 is started. The fact that an artifact was detected as assumed to be an EKG signal which resulted in an impossible variation in the period is assumed to have resulted from having a threshold which is set too high. Therefore, the value of $V_{max}$ is reset to $V_{max}/2$ in block 186. Then another latency period of 250 milliseconds is observed during which incoming data is ignored, and, thereafter, processing returns to test 170. That concludes the learning process.

Figure 24A:
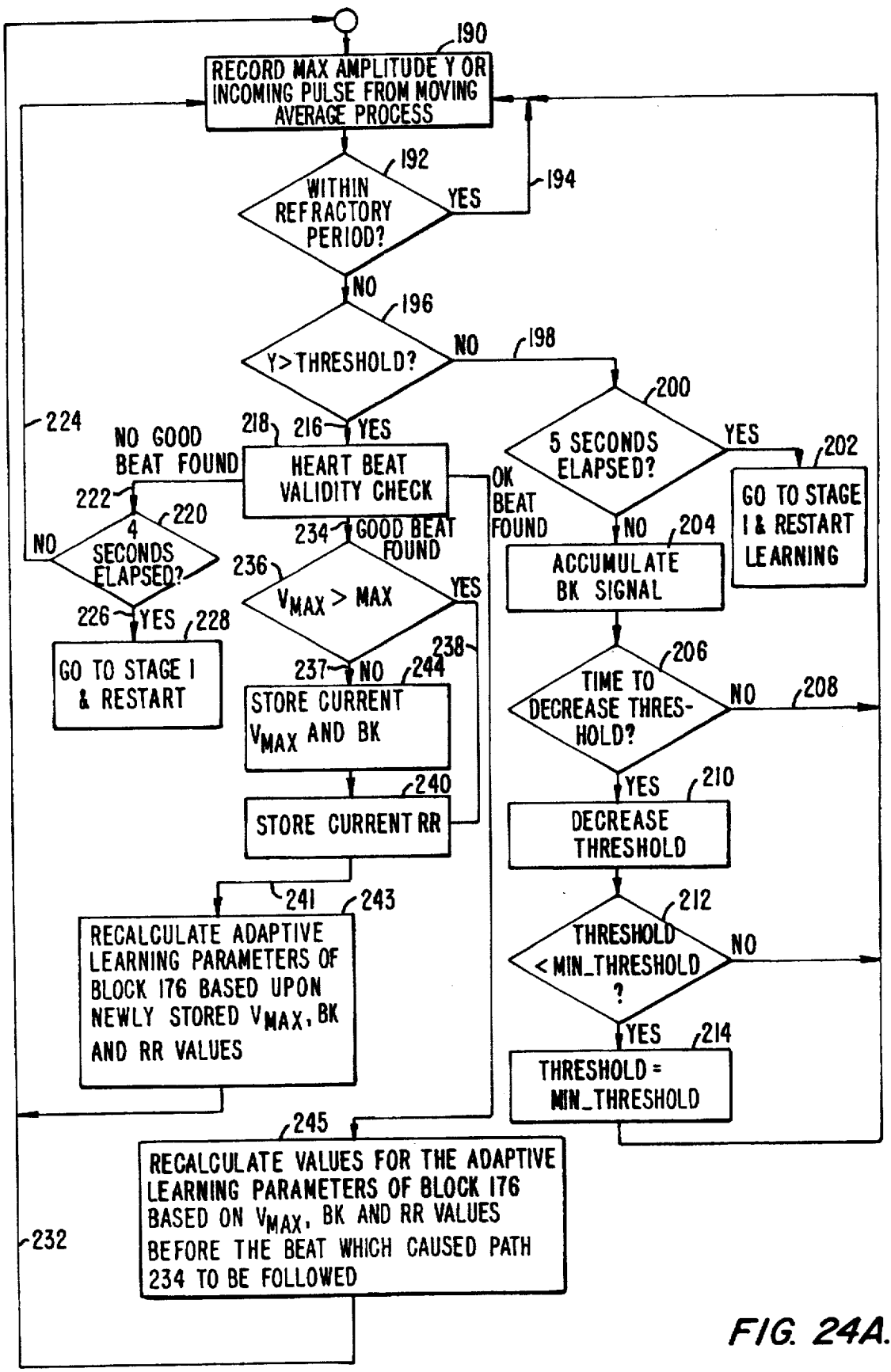
FIG. 24, comprised of FIGS. 24(A) and 24(B), is a detailed flow chart of the preferred embodiment for the heart rate arbitrator process represented by block 150 of FIG. 22.
Figure 24B:
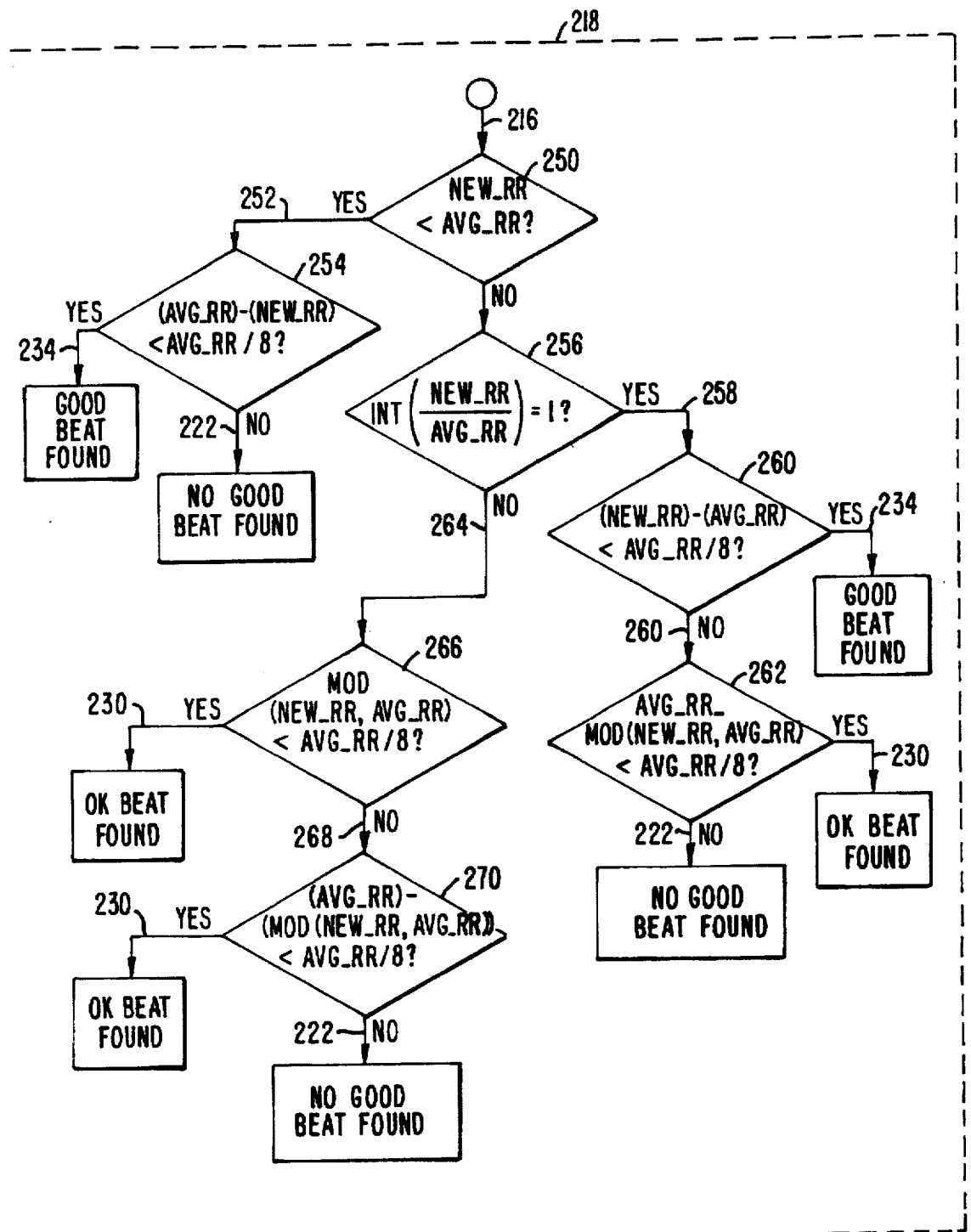

Referring to FIG. 24, comprised of FIGS. 24(A) and 24(B), there is shown a flow chart of the preferred embodiment for the heart rate arbitrator block 150 in FIG. 22. The purpose of the heart rate arbitrator is to determine which of the pulses in the incoming data are EKG pulses. The process starts with block 190 where the value of the maximum amplitude Y in any pulse in the incoming data from the moving averager is determined and is recorded. If that pulse was within the refractory period, as tested by test 192, then the value for its maximum amplitude Y is ignored as symbolized by path 194. If the pulse was not within the refractory period, test 196 is performed to determine if the Y value of the pulse being processed is greater than the threshold currently being used for pulse discrimination. This threshold value is adaptive and is changed at steps to be described below under certain conditions.

If test 196 determines that the Y value of the pulse currently being processed is not greater than the threshold value, branch 198 is taken because it is likely that the adaptive threshold will have to be decreased because a legitimate EKG pulse was missed. Processing along branch 198 includes starting a timer at block 200 and testing in block 200 whether 5 seconds has elapsed. If it has, processing is vectored by block 202 back to the start of the learning process at block 160 in FIG. 23(A) to relearn the characteristics of this user's EKG waveform. If test 200 concludes that 5 seconds has not elapsed, then the process of block 204 is performed to accumulate and average the background noise from the sample values outside the refractory period (adding the sample values after the refractory period before the next Y value comes along and divide by the number of samples so accumulated) so as to be able to update the value of the variable BK if necessary. This process is symbolized by block 204.

Next, test 206 determines whether a sufficient amount of time has passed to warrant decreasing the threshold. The amount of time to wait can be a default value or it can be adaptive. If an insufficient amount of time has passed, processing returns to block 190 to record a new Y, as symbolized by path 208. If a sufficient amount of time has passed to warrant decreasing the adaptive threshold, block 210 is performed to decrease the threshold by an amount equal to the Step_Threshold variable set in block 176 of the learning process.

Test 212 is performed after the threshold is lowered to determine if the adaptive threshold is still greater than the variable Min_Threshold set in block 176 of the learning process. If not, processing returns to block 190 to record a new $V_{max}$. If the adaptive threshold is less than Min_Threshold, step 214 is performed to adjust the adaptive threshold to the value of Min_Threshold, and then processing returns to block 190 to record a new Y value. Anytime processing returns to block 190, the input data is being scanned for a new peak and is tested in test 196 to see if it exceeds the current value for the adaptive threshold. If no pulses are seen, the adaptive threshold keeps decreasing down to the value of Min_Threshold until branch 216 is taken out of test 196 indicating that a new pulse has a Y value that exceeds the threshold.

Next, step 218 is performed to determine the validity of the new candidate heart beat pulse found in test 196. The processing of step 218 is detailed in the flow chart of FIG. 24(B) to be discussed below. If the validity check of block 218 finds no good beat, test 220 is performed to determine if 4 seconds has elapsed with no good beat being found. In other words test 220 starts a timer the first time path 222 is taken, and loops back to block 190 via path 224 to look for a new pulse. If the paths 216 and 222 and 224 are taken for 4 consecutive seconds with no good beat being found, path 226 is taken to block 228 where processing is vectored back to stage 1, i.e., block 160 in FIG. 23(A) to restart the learning process.

If the heart beat validity check of block 218 finds a beat which is of marginal quality but not good enough to update the RR variable, processing is vectored back via path 230 and 232 to block 190 to look for another pulse in new data. Path 230 is taken when an EKG beat was not found when expected, i.e., after the latency period, but a new EKG beat is still to be looked for using the same adaptive threshold and latency period.

If the heart beat validity check of block 218 finds a beat which is good, path 234 is taken to test 236 where the Y value of the pulse is set as the new $V_{max}$ value and to determine if the new $V_{max}$ is greater than the default variable MAX. If it is, the peak is probably an artifact that occurs in the window during which EKG pulses are expected. In such a case, processing is vectored via path 238 to the processing of block 240 so as to skip the processing of block 244. In block 240, the current RR value is stored for the new beat which has been found or for what whatever pulse cause the test of block 236 to return a yes response and cause path 238 to be traversed. In some alternative embodiments, processing will be vectored along path 238 to point 242 and thence via path 232 to block 190.

If the test of block 236 determines that the new $V_{max}$ value is less than the default variable MAX, the beat is probably a good beat, and the path 237 is taken to the processing of block 244. The processing of block 244 stores the new $V_{max}$ value and the most recent BK background noise level point in a ring buffer for later computation of new averages for both these values. Then the processing of block 240 is performed to store the current RR value for the new beat. If path 237 was taken out of test 236 through the processes of block 244 and 240, processing is vectored on path 241 to the processing of block 243.

The processing of block 243 calculates a new average $V_{max}$ and a new average BK value based upon the 8-12 values currently residing in the ring buffer. These new averages and the new RR value stored in block 240 are used to calculate the values of the adaptive learning parameters defined by the equations listed in block 176.

If, on the other hand, the heart beat validity check process of block 218 results in a conclusion that the beat currently being process is classified as only "OK", then path 230 is taken to the processing of block 245. Block 245 calculates a new average $V_{max}$ and a new average BK value based upon the 8-12 values currently residing in the ring buffer without the addition of the new $V_{max}$ and BK values resulting from the new OK beat. These $V_{max}$ and BK averages thus calculated and the currently existing RR value are used to recalculate the values of the adaptive learning parameters defined by the equations listed in block 176. After the processing of either block 243 or 245, processing is vectored by path 232 to block 190 to start processing of the next beat.

Referring to FIG. 24(B), there is shown a flow chart of the processing that is carried out in block 218 of FIG. 24(A) to determine if the pulse found after the current value for the refractory period RP, i.e., during the window when the next EKG pulse is expected, is a valid EKG pulse or not. The processing of FIG. 24(B) is reached only after learning has been successfully accomplished and all the parameters of block 176 in FIG. 23(B) have been set and a new pulse has been found outside the refractory period which has a $V_{max}$ value which is greater than the current value for the adaptive threshold.

The first step in the validity checking process is determining whether the heart rate interval RR for the new beat is smaller than the average heart rate interval. To accomplish this first test, the processing of test 250 is performed to set the value of a variable New_RR at the heart rate interval for the new beat and compare New_RR to an average heart rate interval Avg_RR computed in block 240 on a previous pass through the processing of that block. If New_RR is less than Avg_RR, path 252 is taken to test 254 where it is determined if [(Avg_RR) minus (New_RR)] is less than (Avg_RR)/8. If it is, then path 234 is taken to test 236 in FIG. 24(A). If not, path 222 is taken to test 220 in FIG. 24(A). In other words, test 254 calls the new pulse a good beat if the difference between New_RR and Avg_RR is less than one-eighth the Avg_RR, and, if not, calls it a bad beat on grounds that the pulse rate has changed too drastically from the average. This an implementation of a rule of reason which rejects any alleged EKG pulse if its timing represents a heart rate which changed by more than 12.5% of the average heart rate from the last EKG pulse.

Returning to the consideration of test 250, if the new heart rate New_RR is greater than the average heart rate Avg_RR, indicating the heart is slowing down, then a rule of reason analysis is performed to determine if the slow down is a reasonable amount. To perform part of this analysis, test 256 ascertains the integer portion of the ratio (New_RR/Avg_RR). If the integer portion of this ratio is 1, path 258 is taken to test 260. Test 260 determines whether the difference between New_RR and Avg_RR is less than (Avg_RR)/8. If it is, path 234 is taken to test 236 in FIG. 24(A). If not path 260 is taken to test 262 where it is determined if the difference between Avg_RR and the remainder of the ratio [(New_RR)/(Avg_RR)] is less than one-eighth of Avg_RR. If it is, then the beat is determined to be an "OK" beat, and path 230 is taken to point 242 in FIG. 24(A) to return to block 190 to start looking for a new beat using the same adaptive threshold level and other learned parameters as were used on the last pass through the processing of FIG. 24(A). If the difference between Avg_RR and the remainder of the ratio [(New_RR)/(Avg_RR)] is not less than one-eighth of Avg_RR, then the pulse is deemed to be an artifact, and path 222 is taken to test 220 in FIG. 24(A).

Returning to the consideration of test 256, if the new heart rate established by the new candidate peak is found in test 256 to be more than twice as slow as the average heart rate, path 264 is taken to test 266 where it is determined whether or not this fact resulted simply from missing one EKG pulse. More precisely, test 266 determines if the remainder of the ratio [(New_RR)/(Avg_RR)] is less than one-eighth of Avg_RR. If it is, then the vastly slower heart rate is probably caused by a missed EKG pulse, and path 230 is taken to point 242 in FIG. 24(A) to return to block 190 to begin looking for a new pulse. In alternative equivalent embodiments, path 230 leads to block 210 in FIG. 24(A) rather than point 242 so as to decrease the threshold and start again looking for a new peak. If test 266 finds that the remainder of the ratio [(New_RR)/(Avg_RR)] is greater than one-eighth of Avg_RR, then path 268 is taken to test 270. Test 270 determines whether the difference between Avg_RR and the remainder of the ratio [(New_RR)/(Avg_RR)] is less than one-eighth of Avg_RR. If it is, the slower heart rate is assumed to have been caused by a missed EKG pulse, and path 230 is taken to the OK beat processing steps 242 (or block 210 in alternative embodiments) as described above. If the difference between Avg_RR and the remainder of the ratio [(New_RR)/(Avg_RR)] is not less than one-eighth of Avg_RR, the new peak is deemed to be an artifact, and path 222 is taken to test 220 in FIG. 24(A).

Figure 25:
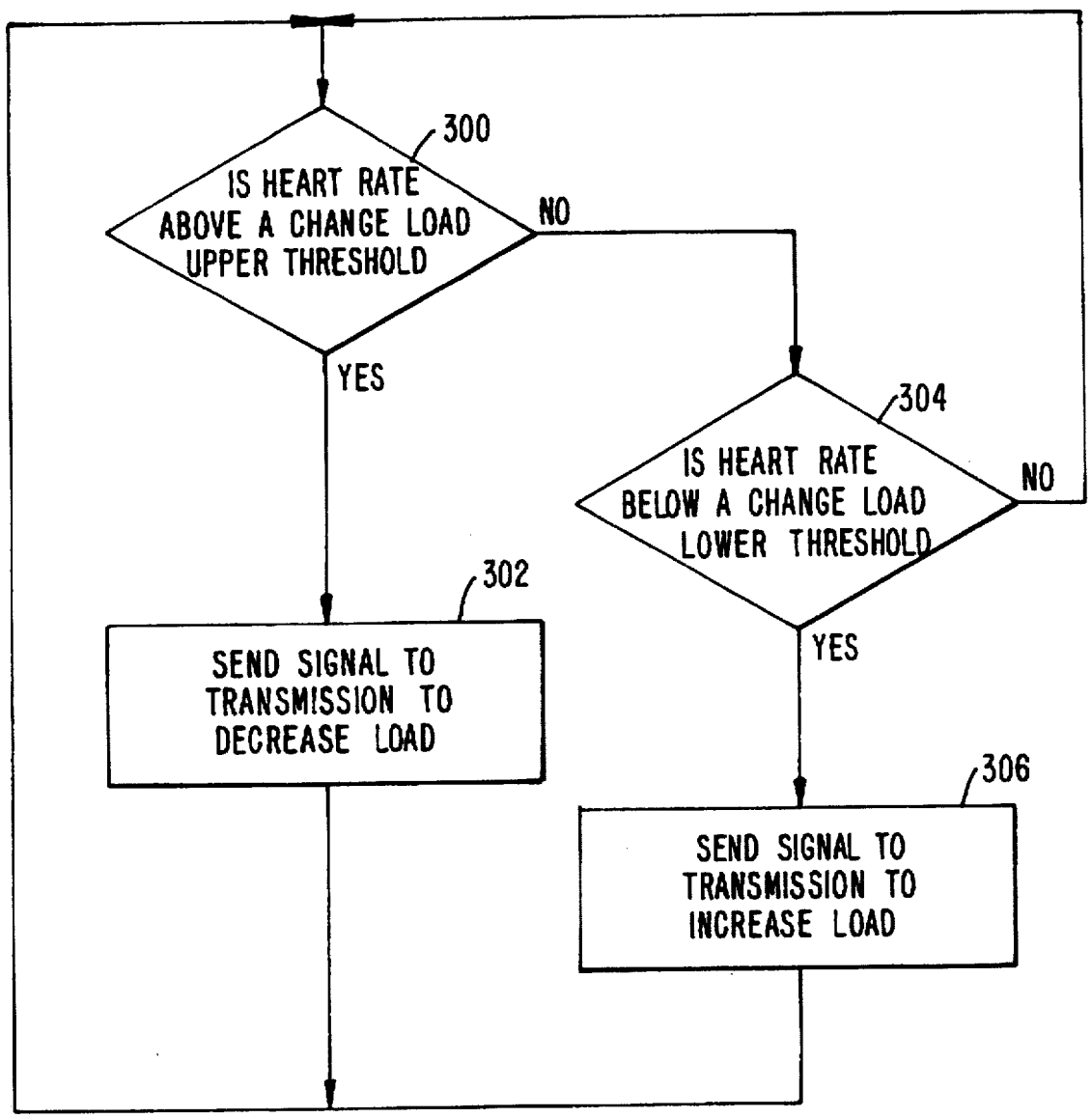
FIG. 25 is a flow chart for a process of using the measure heart rate to control the load resisting movements by the user in an exercise or outdoor bike.

Referring to FIG. 25, there is shown a flow chart of a process that is implemented in some embodiments to automatically change the load of an exercise machine based on a determination of the heart rate of the exerciser so as to safely maintain the heart rate within predetermined safe limits. The process is linked to the process for determining the heart rate of the user either as part of it or linked by virtue of shared data. Specifically, the process of FIG. 25 can be a subroutine or a separate program execution of which can be enabled or disabled by the user or which can be enabled all the time. Either the subroutine or separate program communicates with the heart rate enabling program by shared memory, i.e., the load variation program knows where the calculated heart rate data is stored and can access that memory or register. The first step in the automatic load variation program is symbolized by block 300. This test reads the calculated heart rate and compares it to a change load upper threshold. The change load upper threshold can be set automatically according to aerobic effect target range data based upon the age and weight of the user. The age and weight data may be entered as configuration data when the exercise machine is set up or, preferably, entered interactively each time the user logs on for an exercise session. Alternatively, the upper threshold can be a programmable number which is interactively under the user's control and which can be changed at any time. If test 300 determines that the measured heart rate is greater than the upper threshold, the process of block 302 is performed to send a signal to an automatic transmission or transducer to cause mechanical or electrical changes in the exercise machine to decrease the load. Thereafter processing vectors back to test 300.

If test 300 determines that the measured heart rate is below the upper threshold, test 304 is performed to determine if the measured heart rate is below a change load lower threshold. The change load lower threshold can be set automatically according to aerobic effect target range data based upon the age and weight of the user. The age and weight data may be entered as configuration data when the exercise machine is set up or, preferably, entered interactively each time the user logs on for an exercise session. Alternatively, the upper threshold can be a programmable number which is interactively under the user's control and which can be changed at any time. If test 304 determines that the measure heart rate is below the lower threshold, the process of block 306 is performed to send a signal to an automatic transmission or transducer to cause mechanical or electrical changes in the exercise machine to increase the load. Thereafter processing vectors back to test 300. If test 304 determines that the measured heart rate is above the lower threshold, processing vectors to test 300 to start the monitoring process over again.

Referring to FIG. 26, there is shown an automatic digital gain control embodiment in the form of an alternative embodiment for block 214 in FIG. 24(A). In this automatic gain control embodiment, processing is as described with reference to FIGS. 7, 22 and 23(A) and (B) and 24(A) and (B) except that the processing of block 214 in FIG. 24(A) is replaced with the processing of FIG. 26. In the automatic gain control embodiment, if the test 212 determines that the threshold is less than the minimum threshold. If it is, then the gain control number 64 in the equation of FIG. 16 is changed to a smaller number to increase the amplitude of the running average. Then the threshold is set equal to the value of the variable Min_Threshold set by the learning process, and processing continues as previously described.

Referring to FIG. 27, there is shown an alternative embodiment for an electrode arrangement on the handlebars of an outdoor bike, an exercise bike etc. In this arrangement, the handlebar grips 300 and 302 each have two removable snap-in electrodes and receivers mounted thereon, of which, button 304 is typical. FIG. 28 shows, in cross section, the configuration of the removable button electrodes. Each electrode such as electrode 304 is comprised of a conductive button 306 with a rounded surface 308 on top and a snap-in projection 310 on the bottom. The snap-in portion 310 is received in a well 312 of a receiver portion 314 which also is made of a conductive material and which is coupled to a wire 316 that is coupled to the electronics of the heart rate monitor. The snap-in button configuration for the electrodes 304 is only one embodiment which is preferred for use when riders use the type of gloves shown in FIGS. 30A and 30B. For riders who ride bare handed, the snap-in button configuration can be eliminated and the buttons 306 can be permanently affixed to the receiver 314 or the electrode can be formed as one piece with the same curved top surface 308. In some embodiments, the entire receiver portion 314 is electrically conductive, whereas in other embodiments, only a portion of the receiver portion in physical contact with the removable button portion is conductive, and this portion is electrically connected to wire 316 such that electrical continuity from the users palm to said heart rate monitor is achieved and maintained.

Referring to FIG. 29, there is shown a side view of a snap ring mount for mounting the electrodes of the type shown in FIG. 28 or of a single unit construction to the handlebars of bikes or other exercise machines. This type mount uses a spring steel or plastic ring 318 which has a diameter slightly smaller than the diameter of the handlebar to which the electrode is to be attached. The ring 318 has an opening 320 which is large enough relative to the flexibility of the ring 318 to allow the ring to be expanded temporarily so as to slip it over the circular form of the handlebars. Preferably, the relative diameters of the ring 318 in the resting state versus the diameter of the handlebar to which it is to be attached and the spring constant and coefficient of friction of the ring will be sufficient to prevent the ring from spinning on the handlebar after it is attached. At the top center of the ring 318, the button electrode and its receiver 314 are affixed to the ring. More precisely, the receiver 314 is affixed to the ring 318, and the button electrode is snapped into the receiver is some embodiments or permanently affixed to the receiver in other embodiments.

Referring to FIG. 30A and 30B, there are shown, respectively, a top view and a bottom view of special outdoor bike rider gloves with built-in snap-in button electrodes. In these gloves, two metal strips electrodes 322 and 324 are affixed to the inside surface of each glove. These metal strip electrodes make electrical contact with the hands of the rider. Electrically connected to and physically attached to these metal strip electrodes are two snap-in button electrodes 306A and 306B. These snap-in electrodes have their curved surfaces facing the palms of the rider's hands and have their snap-in projections 310 facing away from the rider's palm. In use, the rider aligns these snap-in projections 310 with receiver portions 314 mounted on the grips of the handlebars of the bike or other exercise machine. In some embodiments, the handle grips of the bike will be movable within a certain range of rotations and sliding axially along the handlebar so as to not require the rider to keep his or her hands in one place on the handlebars.

Although the invention has been described in terms of the preferred and alternative embodiments described herein, those skilled in the art will appreciate numerous alternative hardware and software architectures that can be used to implement the teachings of the invention. All such alternative architectures are intended to be included within the scope of the claims appended hereto.

What is claimed is:

1. A heart rate monitor for sensing EKG signals and displaying a heart rate based upon the frequency of occurrence of ORS complexes in said EKG waveform, comprising:

at least two electrical contacts for making electrical contact with different areas of a user's body;

an amplifier coupled to said at least two electrical contacts for amplifying any signals picked up by said contacts and suppressing any common mode noise;

a plurality of bandpass filters coupled to receive the output of said amplifier, each bandpass filter having a passband from approximately 5 to 40 Hertz, each said bandpass filter comprising a low pass analog filter having a first order rolloff characteristic with a corner frequency between 25 and 40 Hertz, and a high pass analog filter having a second order rolloff characteristic with a corner frequency between 5 and 15 Hertz;

an amplifier coupled to receive the output of said bandpass filter(s);

an analog-to-digital converter coupled to receive the output signal of said amplifier and convert said output signal to a plurality of digital samples;

a computer coupled to receive said digital samples and programmed to process said digital samples by digitally filtering said samples to suppress frequencies below about 5–15 Hertz and to suppress frequencies of about 25–40 Hertz and above to generate filtered data, and programmed to process said filtered data so as to suppress artifacts while enhancing or at least not suppressing R peaks in QRS waveforms in EKG signals picked up by said electrical contact and encoded in said filtered data to generate enhanced data, and programmed to process said enhanced data to find R peaks therein which have a heart rate period which is within a range from about 40 to about 220 beats per minute and which is not changing by more than about 12.5% between adjacent beats, and programmed to learn the background noise characteristics of the enhanced data and the maximum amplitude and heart rate period characteristics of said R peaks so located in said enhanced data and programmed to set the level of an adaptive discrimination threshold using said learned characteristics, and, after said characteristics are learned, programmed to use said adaptive threshold to locate further candidate peaks in new incoming enhanced data which are possibly R peaks in a QRS complex and subject said candidate peaks to a plurality of validity tests to determine which candidate peaks are probably actual R peaks and programmed to compute an average maximum amplitude and an average heart rate period and a refractory period for a plurality of R peaks that pass said validity tests, and to use the results of at least said average maximum amplitude computation to adjust the level of said adaptive discrimination threshold and said refractory period, and to continue to compute a running average maximum amplitude and a running average heart rate period and new refractory periods for each new R peak that passes said validity tests on an ongoing basis, and for outputting for display heart rate data encoding at least said head rate period, said validity tests to which candidate peaks are subjected including at least a test to determine whether the new heart rate period which is defined by a new candidate peak represents more than a predetermined change from the average head rate period previously determined;

a display coupled to receive said head rate data from said computer and to display a head rate indication encoded in said head rate data* and further comprising a wristwatch housing said heart rate monitor, said wristwatch having a face a back, and wherein said said at least two electrical contacts comprise three electrical contacts and wherein at least two of said three electrical contacts are on said face of said wristwatch and wherein at least one of said three electrical contact is on said back of said wristwatch.

2. A heart rate monitor for sensing EKG signals and displaying a heart rate based upon the frequency of occurrence of QRS complexes in said EKG waveform, comprising:

at least two electrical contacts for making electrical contact with different areas of a user's body;

an amplifier coupled to said at least two electrical contacts for amplifying any signals picked up by said contacts and suppressing any common mode noise;

a plurality of bandpass filters coupled to receive the output of said amplifier, each bandpass filter having a passband from approximately 5 to 40 Hertz, each said bandpass filter comprising a low pass analog filter having a first order rolloff characteristic with a corner frequency between 25 and 40 Hertz, and a high pass analog filter having a second order rolloff characteristic with a corner frequency between 5 and 15 Hertz;

an amplifier coupled to receive the output of said bandpass filter(s);

an analog-to-digital converter coupled to receive the output signal of said amplifier and convert said output signal to a plurality of digital samples;

a computer coupled to receive said digital samples and programmed to process said digital samples by digitally filtering said samples to suppress frequencies below about 5–15 Hertz and to suppress frequencies of about 25–40 Hertz and above to generate filtered data, and programmed to process said filtered data so as to suppress artifacts while enhancing or at least not suppressing R peaks in QRS waveforms in EKG signals picked up by said electrical contact and encoded in said filtered data to generate enhanced data, and programmed to process said enhanced data to find R peaks therein which have a heart rate period which is within a range from about 40 to about 220 beats per minute and which is not changing by more than about 12.5% between adjacent beats, and programmed to learn the background noise characteristics of the enhanced data and the maximum amplitude and heart rate period characteristics of said R peaks so located in said enhanced data and programmed to set the level of an adaptive discrimination threshold using said learned characteristics, and, after said characteristics are learned, programmed to use said adaptive threshold to locate further candidate peaks in new incoming enhanced data which are possibly R peaks in a QRS complex and subject said candidate peaks to a plurality of validity tests to determine which candidate peaks are probably actual R peaks and programmed to compute an average maximum amplitude and an average heart rate period and a refractory period for a plurality of R peaks that pass said validity tests, and to use the results of at least said average maximum amplitude computation to adjust the level of said adaptive discrimination threshold and said refractory period, and to continue to compute a running average maximum amplitude and a running average heart rate period and new refractory periods for each new R peak that passes said validity tests on an ongoing basis, and for outputting for display heart rate data encoding at least said heart rate period, said validity tests to which candidate peaks are subjected including at least a test to determine whether the new heart rate period which is defined by a new candidate peak represents more than a predetermined change from the average heart rate period previously determined;

a display coupled to receive said heart rate data from said computer and to display a heart rate indication encoded in said heart rate data and further comprising an exercise machine housing said heart rate monitor and having a control panel having a front surface and wherein said at least two electrical contacts comprise three electrical contacts and wherein at least two of said three electrical contacts are located on said exercise machine in a position which can be easily reached by one hand of a user who is using said exercise machine to exercise and at least one of said three electrical contacts is located on said exercise machine in a position which can be easily reached by the other hand of said user.

3. A head rate monitor for sensing EKG signals and displaying a heart rate based upon the frequency of occurrence of QRS complexes in said EKG waveform, comprising:

at least two electrical contacts for making electrical contact with different areas of a user's body;

an amplifier coupled to said at least two electrical contacts for amplifying any signals picked up by said contacts and suppressing any common mode noise;

a plurality of bandpass filters coupled to receive the output of said amplifier, each bandpass filter having a passband from approximately 5 to 40 Hertz, each said bandpass filter comprising a low pass analog filter having a first order rolloff characteristic with a corner frequency between 25 and 40 Hertz, and a high pass analog filter having a second order rolloff characteristic with a corner frequency between 5 and 15 Hertz;

an amplifier coupled to receive the output of said bandpass filter(s);

an analog-to-digital converter coupled to receive the output signal of said amplifier and convert said output signal to a plurality of digital samples;

a computer coupled to receive said digital samples and programmed to process said digital samples by digitally filtering said samples to suppress frequencies below about 5–15 Hertz and to suppress frequencies of about 25–40 Hertz and above to generate filtered data, and programmed to process said filtered data so as to suppress artifacts while enhancing or at least not suppressing R peaks in QRS waveforms in EKG signals picked up by said electrical contact and encoded in said filtered data to generate enhanced data, and programmed to process said enhanced data to find R peaks therein which have a heart rate period which is within a range from about 40 to about 220 beats per minute and which is not changing by more than about 12.5% between adjacent beats, and programmed to learn the background noise characteristics of the enhanced data and the maximum amplitude and heart rate period characteristics of said R peaks so located in said enhanced data and programmed to set the level of an adaptive discrimination threshold using said learned characteristics, and, after said characteristics are learned, programmed to use said adaptive threshold to locate further candidate peaks in new incoming enhanced data which are possibly R peaks in a QRS complex and subject said candidate peaks to at plurality of validity tests to determine which candidate peaks are probably actual R peaks and programmed to compute an average maximum amplitude and an average heart rate period and a refractory period for a plurality of R peaks that pass said validity tests, and to use the results of at least said average maximum amplitude computation to adjust the level of said adaptive discrimination threshold and said refractory period, and to continue to compute a running average maximum amplitude and a running average head rate period and new refractory periods for each new R peak that passes said validity tests on an ongoing basis, and for outputting for display head rate data encoding at least said heart rate period, said validity tests to which candidate peaks are subjected including at least a test to determine whether the new heart rate period which is defined by a new candidate peak represents more than a predetermined change from the average heart rate period previously determined;

a display coupled to receive said heart rate data from said computer and to display a heart rate indication encoded in said heart rate data and further comprising an exercise machine housing said heart rate monitor and having a handlebar which is normally grasped by two hands of a user using said exercise machine to exercise during said exercise and wherein said at least two electrical contacts comprise three electrical contacts at least two of said three electrical contacts being located at a position on said handlebar which is normally in contact with one hand of a user who is using said machine to exercise and at least one of said three electrical contacts located at a position on said handle which is normally in contact with the other hand of a user who is using said machine to exercise.

4. A heart rate monitor comprising:

a chest strap having a first surface which contacts the chest of a user, said first surface having at least three electrical contacts thereon and wherein said at least three electrical contacts are mounted on said first surface of said chest strap so as to contact the check of said user, and said chest strap further comprising a heart rate processing unit including a radio frequency transmitter, said heart rate processing unit comprising:

a differential amplifier coupled to said at least three electrical contacts for amplifying any signals picked up by said contacts and suppressing any common mode noise;

an analog bandpass filter coupled to receive the output of said differential amplifier and having a passband from approximately 5 to 40 Hertz; an amplifier coupled to receive the output of said bandpass filter;

an analog-to-digital converter coupled to receive the output signal of said amplifier and convert said output signal to a plurality of digital samples, said analog-to-digital converter having a sampling rate which is a multiple of 60 Hertz;

a computer coupled to receive said digital samples and programmed to process said digital samples by digitally filtering said samples to suppress frequencies below about 5-10 Hertz and to suppress frequencies about 40-60 Hertz and above to generate filtered data, and programmed to process said filtered data so as to suppress artifacts while enhancing or at least not suppressing R peaks in QRS waveforms in EKG signals picked up by said electrical contact and encoded in said filtered data to generate enhanced data, and programmed to process said enhanced data to find R peaks therein which have a heart rate period which is within a range from about 40 to about 220 beats per minute and which is not changing by more than about 12.5% between adjacent beats, and programmed to learn the background noise characteristics of the enhanced data and the maximum amplitude and heart rate period characteristics of said R peaks so located in said enhanced data and programmed to set the level of an adaptive discrimination threshold using at least said learned maximum amplitude characteristics, and, after said characteristics are learned, programmed to use said adaptive threshold to locate further candidate peaks in new incoming enhanced data which are possibly R peaks in a QRS complex and subject said candidate peaks to a plurality of validity tests to determine which candidate peaks are probably actual R peaks and programmed to perform computations to determine an average maximum amplitude and an average heart rate period and a refractory period for a plurality of R peaks that pass said validity tests, and to use the results of at least said average maximum amplitude computations to adjust the level of said adaptive discrimination threshold and said refractory period, and to continue to compute a running average maximum amplitude and a running average heart rate period and new refractory periods for each new R peak that passes said validity tests on an ongoing basis, and for outputting for display heart rate data encoding at least said heart rate period, said validity tests to which candidate peaks are subjected including at least tests to determine whether the new heart rate period which is defined by new candidate peaks represents more than a predetermined change from the average heart rate period previously determined;

and wherein said radio frequency transmitter on said chest strap is coupled to receive said heart rate information from said computer and modulate said heart rate information onto a radio frequency carrier and transmit said carrier;

and further comprising a display unit including a radio frequency receiver for receiving said radio frequency carrier transmitted by said radio frequency transmitter on said chest strap and demodulating said carrier to derive said heart rate information and displaying said heart rate information.

5. An apparatus for determining heart rate from electrical signals generated within a body, comprising:

at least three electrical contacts for detecting said electrical signal .s when placed in contact with said body;

a differential amplifier having a gain of from approximately 5-10 coupled to said electrical contacts for amplifying any signals detected by said electrical contact means and suppressing any common mode noise;

an analog bandpass filter coupled to receive the output of said differential amplifier and having a passband from approximately 5 to 40 Hertz, said bandpass filter comprising a low pass analog active filter having a first order rolloff characteristic with a corner frequency between 25 and 40 Hertz, and a high pass analog active filter having a second order rolloff characteristic with a corner frequency between 5 and 15 Hertz;

an analog-to-digital converter coupled to receive an analog output signal from said analog passband filter and convert said analog signal to a plurality of digital samples using a sample rate that is a multiple of the powerline Ac voltage frequency;

a digital filter for receiving said digital samples and suppressing noise signals that have a frequency of 60 Hertz and further suppressing signals that have frequencies below about 5-15 Hertz and above about 25-40 Hertz to generate filtered data, said digital filter being a recursive filter having integer coefficients so as to speed up the digital filtering process;

an enhancement signal processor to receive said filtered data and maintain or increase the amplitude of signals therein that have predetermined characteristics of QRS complexes in human heartbeat signals so as to generate enhanced digital data;

a post-processing heart rate determination signal processor means for analyzing said enhanced digital data and determining the heart rate therefrom;

a display for displaying said heart rate determined by said post-processing heart rate determination signal processor means.

6. The apparatus of claim 5 wherein said enhancement signal processor comprises:

a differentiator for determining the slope of peaks in said filtered data and generating a slope signal which defines the magnitude and sign of the slopes of each portion of each said peak;

a squaring processor for squaring the results from said differentiator by looking up said results in a lookup table giving the squares of possible values that could be output from said differentiator;

a moving average processor for computing a moving average of said positive values only signal and outputting a moving average signal which defines said moving average over time.

7. The apparatus of claim 5 wherein said enhancement signal processor comprises:

means for slicing each peak in said filtered data into a plurality of slices, each slice taken at a different amplitude level with the highest amplitude slice taken at or near the peak amplitude of said peak and the lowest amplitude slice taken somewhere at or above the baseline of the peak, and wherein each slice is comprised of a plurality of timeslots, each timeslot storing a digital data bit, said digital data bits each representing a different time at the amplitude level represented by said slice, some of said data bits being in a first logic state and some of said data bits being in a second state, said data bits in said first logic state representing points inside the envelope of a peak in a signal defined by said filtered data from said digital filter and said data bits in said second logic state representing points outside the envelope of a peak in a signal defined by said filtered data from said digital filter;

means for matching the data written into the timeslots of each slice on a bit for bit basis to corresponding bits stored in a logic template having one row for every slice and the same number of bits in each row as there are timeslots in each slice, and wherein the data in said logic template defines the shape of an ideal QRS complex of a human heartbeat with data bits in a first logic state at all points inside an envelope defining the shape of said ideal QRS waveform and data bits in a second logic state at all points outside the envelope, said matching being performed using a logical exclusive-or matching operation between each bit in a timeslot in a slice through a peak in the filtered data and a corresponding bit in a row of said logic template and outputting a logic 1 for each match as the data from one slice is processed; and means for counting the number of logic is generated by said means for matching as each slice is processed and generating enhanced digital data which defines the number of logic is generated while processing data from all slices from each peak so processed.

8. An apparatus for determining heart rate from electrical signals generated within a body, comprising:

an electrical contact means including at least three electrical contacts for detecting said electrical signals when placed in contact with said body;

a differential amplifier having a gain of from approximately 5–10 coupled to said electrical contact means for amplifying any signals detected by said electrical contact means and suppressing any common mode noise;

an analog bandpass filter coupled to receive the output of said differential amplifier and having a passband from approximately 5 to 40 Hertz, said bandpass filter comprising a low pass analog active filter having a first order rolloff characteristic with a corner frequency between 25 and 40 Hertz, and a high pass analog active filter having a second order rolloff characteristic with a corner frequency between 5 and 15 Hertz;

an analog-to-digital converter coupled to receive an analog output signal from said analog passband filter and convert said analog signal to a plurality of digital samples using a sample rate that is a multiple of the powerline Ac voltage frequency;

a digital filter for receiving said digital samples and suppressing noise signals that have a frequency of 60 Hertz and further suppressing signals that have frequencies below about 5–15 Hertz and above about 25–40 Hertz to generate filtered data, said digital filter being a recursive filter having integer coefficients so as to speed up the digital filtering process;

an enhancement signal processor to receive said filtered data and maintain or increase the amplitude of signals therein that have predetermined characteristics of QRS complexes in human heartbeat signals so as to generate enhanced digital data;

a post-processing heart rate determination signal processor means for analyzing said enhanced digital data and determining the heart rate therefrom;

a display for displaying said heart rate determined by said post-processing heart rate determination signal processor means; and wherein said enhancement signal processor comprises:

a differentiator for determining the slope of peaks in said filtered data and generating a slope signal which defines the magnitude and sign of the slopes of each portion of each said peak;

a squaring processor for squaring the results from said differentiator by looking up said results in a lookup table giving the squares of possible values that could be output from said differentiator;

a moving average processor for computing a moving average of said positive values only signal and outputting a moving average signal which defines said moving average over time;

and wherein said moving average processor is a computer programmed to compute said moving average in a plurality of iterations and outputting said $Y_N$ iterations as a stream of digital data samples with the most recent digital data sample representing the moving average represented by $Y_N$ and wherein each $Y_N$ iteration output in said moving average data stream is calculated by summing the 8 most recent data samples in said stream of data samples representing said filtered data and dividing the sum by 64.

9. An apparatus for determining heart rate from electrical signals generated within a body, comprising:

an electrical contact means including at least three electrical contacts for detecting said electrical signals when placed in contact with said body;

a differential amplifier having a gain of from approximately 5–10 coupled to said electrical contact means for amplifying any signals detected by said electrical contact means and suppressing any common mode noise;

an analog bandpass filter coupled to receive the output of said differential amplifier and having a passband from approximately 5 to 40 Hertz, said bandpass filter comprising a low pass analog active filter having a first order rolloff characteristic with a corner frequency between 25 and 40 Hertz, and a high pass analog active filter having a second order rolloff characteristic with a corner frequency between 5 and 15 Hertz;

an analog-to-digital converter coupled to receive an analog output signal from said analog passband filter and convert said analog signal to a plurality of digital samples using a sample rate that is a multiple of the powerline Ac voltage frequency;

a digital filter for receiving said digital samples and suppressing noise signals that have a frequency of 60 Hertz and further suppressing signals that have frequencies below about 5–15 Hertz and above about 25–40 Hertz to generate filtered data, said digital filter being a recursive filter having integer coefficients so as to speed up the digital filtering process:

an enhancement signal processor to receive said filtered data and maintain or increase the amplitude of signals therein that have predetermined characteristics of QRS complexes in human heartbeat signals so as to generate enhanced digital data;

a post-processing heart rate determination signal processor means for analyzing said enhanced digital data and determining the heart rate therefrom;

a display for displaying said heart rate determined by said post-processing heart rate determination signal processor means; and wherein said enhancement signal processor comprises:

a differentiator for determining the slope of peaks in said filtered data and generating a slope signal which defines the magnitude and sign of the slopes of each portion of each said peak;

a squaring processor for squaring the results from said differentiator by looking up said results in a lookup table giving the squares of possible values that could be output from said differentiator;

a moving average processor for computing a moving average of said positive values only signal and outputting a moving average signal which defines said moving average over time;

and wherein said differentiator is a digital signal processor programmed to compute the mathematical expression $Y_n/4$, where $Y_n$=represents slope at any particular sample time N, $2X_n$ represents twice the amplitude of the most recent digital data sample from the output of the previous filter, $X_{n-1}$=represents the amplitude of the next most recent digital data sample from the output of the previous filter, $X_{n-3}$=represents the amplitude of the third most recent digital data sample in the stream from the output of the previous filter, and $2X_{n-4}$=represents twice the amplitude of the fourth most recent digital data sample from the output of the previous filter.

10. An apparatus for determining heart rate from electrical signals generated within a body, comprising:

at least three electrical contacts for detecting said electrical signals when placed in contact with said body;

a differential amplifier coupled to said at least three electrical contacts for amplifying any signals detected by said at least three electrical contacts and suppressing any common mode noise;

an analog bandpass filter coupled to receive the output of said differential amplifier and having a passband from approximately 5 to 40 Hertz, said bandpass filter comprising a low pass analog filter having a first order rolloff characteristic with a corner frequency between 25 and 40 Hertz, and a high pass analog filter having a second order rolloff characteristic with a corner frequency between 5 and 15 Hertz;

an analog-to-digital converter coupled to receive an analog output signal from said analog passband filter and convert said analog signal to a plurality of digital samples;

a digital filter for receiving said digital samples and suppressing noise signals that have a frequency of the powerline Ac signal and further suppressing signals that have frequencies below about 5–15 Hertz and above about 25–40 Hertz to generate filtered data, said digital filter being a recursive filter having integer coefficients so as to speed up the digital filtering process;

an enhancement signal processor to receive said filtered data and maintain or increase the amplitude of signals therein that have predetermined characteristics of QRS complexes in human heartbeat signals so as to generate enhanced digital data;

a post-processing heart rate determination signal processor for analyzing said enhanced digital data and determining the heart rate therefrom;

a display for displaying said heart rate determined by said post-processing heart rate determination signal processor.

11. An apparatus for determining heart rate from electrical signals generated within a body, comprising:

at least three electrical contacts for detecting said electrical signals when placed in contact with said body;

a differential amplifier coupled to said at least three electrical contacts for amplifying any signals detected by said at least three electrical contacts and suppressing any common mode noise;

an analog bandpass filter coupled to receive the output of said differential amplifier and having a passband from approximately 5 to 40 Hertz, said bandpass filter comprising a low pass analog filter having a first order rolloff characteristic with a corner frequency between 25 and 40 Hertz, and a high pass analog filter having a second order rolloff characteristic with a corner frequency between 5 and 15 Hertz;

an analog-to-digital converter coupled to receive an analog output signal from said analog passband filter and convert said analog signal to a plurality of digital samples;

a digital filter for receiving said digital samples and suppressing noise signals that have a frequency of the powerline Ac signal and further suppressing signals that have frequencies below about 5–15 Hertz and above about 25–40 Hertz to generate filtered data, said digital filter being a recursive filter having integer coefficients so as to speed up the digital filtering process;

an enhancement signal processor to receive said filtered data and maintain or increase the amplitude of signals therein that have predetermined characteristics of QRS complexes in human heartbeat signals so as to generate enhanced digital data;

a post-processing heart rate determination signal processor for analyzing said enhanced digital data and determining the heart rate therefrom;

a display for displaying said heart rate determined by said post-processing heart rate determination signal processor, and wherein said digital filter includes a recursive low pass filter with a notch at 60 hertz and specified by the equation:

$$Y_n = \tfrac{1}{8}(2Y_{n-1} - Y_{n-2} + X_n - 2X_{n-3} + X_{n-6})$$

where, $Y_n$ represents the output digital sample on each iteration, $Y_{n-1}$ and $Y_{n-2}$ represents previous outputs such that $Y_{n-1}$ represents the most recent previous output while $Y_{n-2}$ represents the second most recent previous output, and wherein x terms such as $X_n$, $X_{n-3}$ and $X_{n-6}$ represent recent raw data inputs such that $X_n$ represents the most recent raw data input, $X_{n-3}$ represents the 3rd most recent raw data input and $X_{n-6}$ represents the 6th most recent raw data input.

12. The apparatus of claim 11 wherein said digital filter includes a recursive bandpass filter with a notch at 60 Hertz and specified by the equation:

$$Y_n = \tfrac{1}{12}(2Y_{n-1} - 3Y_{n-2} + 2Y_{n-3} - Y_{n-4} + X_n - 2X_{n-6} + X_{n-12})$$

where, $Y_n$ represents the output digital sample on each iteration, and $Y_{n-1}$, $Y_{n-2}$, $Y_{n-3}$, and $Y_{n-4}$ represent previous outputs such that $Y_{n-1}$ represents the most recent previous output while $Y_{n-2}$ represents the second most recent previous output, $Y_{n-3}$ represents the fourth most recent previous output and wherein x terms such as $X_n$, $X_{n-6}$ and $X_{n-12}$ represent recent raw data inputs, except that the result of a previous stage's calculation, e.g., $Y_N$ in claim 13, becomes raw data point $X_n$ for the equation given in this claim such that $X_n$ represents the most recent raw data input and is the most recent output sample from the low pass filter defined by claim 13 assuming the low pass filtering process of claim 13 occurs before the bandpass filtering process of this claim, and $X_{n-6}$ represents the 6th most recent data input from the previous stage and $X_{n-12}$ represents the 12th most recent raw data input from the previous stage.

13. An apparatus for determining heart rate from electrical signals generated within a body, comprising:

an electrical contact means including at least three electrical contacts for detecting said electrical signals when placed in contact with said body;

a differential amplifier coupled to said electrical contact means for amplifying any signals detected by said electrical contact means and suppressing any common mode noise;

an analog bandpass filter coupled to receive the output of said differential amplifier and having a passband from approximately 5 to 40 Hertz, said bandpass filter comprising a low pass analog filter having a first order rolloff characteristic with a corner frequency between 25 and 40 Hertz, and a high pass analog filter having a second order rolloff characteristic with a corner frequency between 5 and 15 hertz;

an analog-to-digital converter coupled to receive an analog output signal from said analog passband filter and convert said analog signal to a plurality of digital samples;

a digital filter for receiving said digital samples and suppressing noise signals that have a frequency of the powerline Ac signal and further suppressing signals that have frequencies below about 5–15 hertz and above about 25–40 Hertz to generate filtered data, said digital filter being a recursive filter having integer coefficients so as to speed up the digital filtering process;

an enhancement signal processor to receive said filtered data and maintain or increase the amplitude of signals therein that have predetermined characteristics of QRS complexes in human heartbeat signals so as to generate enhanced digital data;

a post-processing heart rate determination signal processor for analyzing said enhanced digital data and determining the heart rate therefrom;

a display for displaying said heart rate determined by said post-processing heart rate determination signal processor; and wherein said digital filter includes a recursive low pass filter with a notch at 60 hertz and specified by the equation:

$$Y_n = \tfrac{1}{8}(2Y_{n-1} - Y_{n-2} + X_n - 2X_{n-3} + X_{n-6})$$

where, $Y_N$ represents the output digital sample on each iteration, $Y_{n-1}$ and $Y_{n-2}$ represent previous outputs such that $Y_{n-1}$ represents the most recent previous output while $Y_{n-2}$ represents the second most recent previous output, and wherein x terms such as $X_n$, and $X_{n-6}$ represent recent raw data inputs such that $X_n$ represents the most recent raw data input, $X_{n-3}$ represents the 3rd most recent raw data input and $X_{n-6}$ represents the 6th most recent raw data input;

and wherein said digital filter includes a recursive bandpass filter with notch at 60 Hertz and specified by the equation:

$$Y_n = \tfrac{1}{12}(2Y_{n-1} - 3Y_{n-2} + 2Y_{n-3} - Y_{n-4} + X_n - 2X_{n-6} + X_{n-12})$$

where, $Y_N$ represents the output digital sample on each iteration, and $Y_N$ and $Y_{n-4}$ represent previous outputs such that represents the most recent previous output while $Y_{n-1}$ represents the second most recent previous output, $Y_{n-3}$ represents the third most recent previous output, and $Y_{n-4}$ represents the fourth most recent previous output and wherein x terms such as $X_n$, $X_{n-6}$ and $X_{n-12}$ represent recent raw data inputs, except that the result of a previous stage's calculation, becomes raw data point $X_n$ such that $X_n$ represents the most recent raw data input and is the most recent output sample from the low pass filter, and $X_{n-6}$ represents the 6th most recent data input from the previous stage and $X_{n-12}$ represents the 12th most recent raw data input from the previous stage;

and wherein said enhancement signal processor comprises:

a differentiator for determining the slope of peaks in said filtered data and generating a slope signal which defines the magnitude and sign of the slopes on each portion of each said peak;

a squaring processor for squaring said slope signal from said differentiator by looking up said results in a lookup table giving the squares of possible values that could be output from said differentiator;

a moving average processor for computing a moving average of said positive values only signal and outputting a moving average signal which defines said moving average over time.

14. The apparatus of claim 13 wherein said differentiator comprises a digital signal processor which computes the mathematical expression $Y_n=/4$.

where $Y_n$=represents slope at any particular sample time N.

$X_n$=represents twice the amplitude of the most recent digital data sample from the output of the previous filter.

$X_{n-1}$=represents the amplitude of the next most recent digital data sample from the output of the previous filter.

$X_{n-3}$=represents the amplitude of the third most recent digital data sample in the stream from the output of the previous filter, and $2X_{n-4}$=represents twice the amplitude of the fourth most recent digital data sample from the output of the previous filter.

15. The apparatus of claim 14 wherein said moving average processor comprises a computer programmed to compute said moving average as a stream of digital data samples with the most recent digital data sample representing the moving average represented by $Y_N$ and wherein each $Y_N$ in said moving average data stream is calculated by summing the 8 most recent data samples in said stream of data samples representing said filtered data and dividing the sum by 64.

16. A heart rate measurement apparatus for determining heart rate from electrical signals generated within a body, comprising:

an electrical contact means including at least three electrical contacts for detecting said electrical signals when placed in contact with said body;

a differential amplifier coupled to said electrical contact means for amplifying any signals detected by said electrical contact means and suppressing any common mode noise;

an analog bandpass filter coupled to receive the output of said differential amplifier and having a passband from approximately 5 to 40 Hertz, said bandpass filter comprising a low pass analog filter having a first order rolloff characteristic with a corner frequency between 25 and 40 Hertz, and a high pass analog filter having a second order rolloff characteristic with a corner frequency between 5 and 15 Hertz;

an analog-to-digital converter coupled to receive an analog output signal from said analog passband filter and convert said analog signal to a plurality of digital samples;

a digital filter for receiving said digital samples and suppressing noise signals that have a frequency of the powerline Ac signal and further suppressing signals that have frequencies below about 5–15 Hertz and above about 25–40 Hertz to generate filtered data, said digital filter being a recursive filter having integer coefficients so as to speed up the digital filtering process;

an enhancement signal processor to receive said filtered data and maintain or increase the amplitude of signals therein that have predetermined characteristics of QRS complexes in human heartbeat signals so as to generate enhanced digital data;

a post-processing heart rate determination signal processor for analyzing said enhanced digital data and determining the heart rate therefrom;

a display for displaying said heart rate determined by said post-processing heart rate determination signal processor and wherein said apparatus is coupled to an exercise machine having a mechanism which can change the load on the exerciser in response to electrical signals, and further comprising means for comparing said heart rate measured by said heart rate measurement apparatus to upper and lower thresholds of said heart rate at which the degree of load upon the exerciser should be changed so as to maintain the heart rate of the exerciser within a predetermined range, and if the measured heart rate is below the lower threshold, for generating a signal and transmitting said signal to said mechanism so as to cause said mechanism to increase the load on said user, and, if the heart rate measured by the heart rate measurement apparatus is above the upper threshold, generating a signal and transmitting said signal to said transmission so as to cause said transmission to lower the load on said user.

17. A method of detecting a heartbeat rate among unwanted signals such as EMG signals and Ac hum, comprising:

sensing analog signals from a body using electrodes in contact with the skin of the body;

amplifying said analog signals while cancelling common mode noise therein to generate amplified analog signals;

filtering out noise in said amplified analog signals having frequencies below and above the frequency range in which the desired heartbeat rate will lie to generate a filtered signal;

converting the filtered signal to a plurality of digital samples;

digitally filtering the digital samples to remove further remnants of frequencies above and below the range of frequencies in which said heartbeat will lie and to suppress powerline hum at approximately 50–60 hertz so as to generate filtered digital samples;

digitally processing said filtered digital samples to enhance heartbeat peaks in the signals represented by said filtered digital samples to generate enhanced digital samples;

processing said enhanced digital samples to determine said heartbeat rate;

and wherein the step of digitally filtering the digital samples comprises the step of recursively filtering the sample data derived from the signals sensed from said body according to the following recursive filter specifications, for recursively low pass filtering according to the equation:

$$Y_n = \tfrac{1}{8}(2Y_{n-1} - Y_{n-2} + X_n - 2X_{n-3} + X_{n-6})$$

where, $Y_N$ represents the output digital sample on each iteration, $Y_{n-1}$ and $Y_{n-2}$ represent previous outputs such that $Y_{n-1}$ represents the most recent previous output while $Y_{n-2}$ represents the second most recent previous output, and wherein x terms such as $X_n$, $X_{n-4}$ and $X_{n-8}$ represent recent raw data inputs such that $X_n$ represents the most recent raw data input, $X_{n-4}$ represents the 4th most recent raw data and $X_{n-8}$ represents the 8th most recent raw data input, and recursively bandpass filtering according to the equation:

$$Y_n = \tfrac{1}{12}(2Y_{n-1} - 3Y_{n-2} + 2Y_{n-3} - Y_{n-4} + X_n - 2X_{n-6} + X_{n-12})$$

where, $Y_N$ represents the output digital sample of the bandpass filtering step on each iteration, and $Y_{n-1}$ and $Y_{n-2}$ represent previous output digital samples of the bandpass filtering step such that $Y_{n-1}$ represents the most recent previous output while $Y_{n-2}$ represents the second most recent previous output, $Y_{n-3}$ represents the third most recent previous output, and $Y_{n-4}$ represents the fourth most recent previous output and wherein x terms such as $X_n$, $X_{n-6}$ and $X_{n-12}$ represent recent sample inputs such as samples derived from the raw or analog filtered data or digital sample results of a previous stage's calculation such as the digital low pass filtering step, e.g., $Y_N$ output from the digital low pass filter becomes sample $X_n$ for the recursive bandpass filter step defined by the equation given herein, and $X_{n-6}$ represents the 6th most recent data input from the previous stage and $X_{n-12}$ represents the 12th most recent raw data input from the previous stage.

18. A method of detecting a heartbeat rate among unwanted signals such as EMG signals and Ac hum, comprising:

sensing analog signals from a body using electrodes in contact with the skin of the body;

amplifying said analog signals while cancelling common mode noise therein to generate amplified analog signals;

filtering out noise in said amplified analog signals having frequencies below and above the frequency range in which the desired heartbeat rate will lie to generate a filtered signal;

converting the filtered signal to a plurality of digital samples;

digitally filtering the digital samples to remove further remnants of frequencies above and below the range of frequencies in which said heartbeat will lie and to suppress powerline hum at approximately 50–60 Hertz so as to generate filtered digital samples;

digitally processing said filtered digital samples to enhance heartbeat peaks in the signals represented by said filtered digital samples to generate enhanced digital samples;

processing said enhanced digital samples to determine said heartbeat rate; and wherein the step of digitally filtering the digital samples comprises the step of recursively filtering the sample data derived from the signals sensed from said body according to the following recursive filter specifications, for recursively low pass filtering according to the equation:

$$Y_n = \tfrac{1}{8}(2Y_{n-1} - Y_{n-2} + X_n - 2X_{n-3} + X_{n-6})$$

$Y_N$ represents the output digital sample on each iteration, $Y_{n-1}$ and $Y_{n-2}$ represent previous outputs such that $Y_{n-1}$ represents the most recent previous output while $Y_{n-2}$ represents the second most recent previous output, and wherein x terms such as $X_n$, $X_{n-3}$ and $X_{n-6}$ represent recent raw data inputs such that $X_n$ represents the most recent raw data input, $X_{n-3}$ represents the 3rd most recent raw data input and $X_{n-6}$ represents the 6th most recent raw data input, and recursively bandpass filtering according to the equation:

$$Y_n = \tfrac{1}{12}(2Y_{n-1} - 3Y_{n-3} - Y_{n-4} + X_n - 2X_{n-6} X_{n-12})$$

$Y_n$ represents the output digital sample of the bandpass filtering step on each iteration, and $Y_{n-1}$ and $Y_{n-4}$ represent previous output digital samples of the bandpass filtering step such that $Y_{n-1}$ represents the most recent previous output while $Y_{n-2}$ represents the second most recent previous output, $Y_{n-3}$ represents the third most recent previous output, and $Y_{n-4}$ represents the fourth most recent previous output and wherein X terms such as $X_n$, $X_n$, $X_{n-6}$ and $X_{n-12}$ represent recent sample inputs such as samples derived from the raw or analog filtered data or digital sample results of a previous stage's calculation such as the digital low pass filtering step, e.g., $Y_n$ output from the digital low pass filter becomes sample $X_n$ for the recursive bandpass filter step defined by the equation given herein, and $X_{n-6}$ represents the 6th most recent data input from the previous stage and $X_{n-12}$ represents the 12th most recent raw data input from the previous stage and wherein said process of digitally enhancing comprises:

using a computer programmed to differentiate the samples output from said recursive bandpass filter to determine the slope of peaks encoded in said digital sample data, and outputting differentiator digital samples encoding the results of said differentiating operation;

using a computer programmed to square the amplitude of signals encoded in said differentiator digital samples by looking up the squares in a lookup table so as to generate squared digital samples; and using a computer programmed to compute the moving average of said squared digital samples.

19. The process of claim 18 wherein said step of using a computer to calculate said moving average comprises:

using a computer programmed to calculate a moving average of said squared digital samples according to the mathematical expression by adding a plurality of digital samples and dividing the total by the number of samples so added or dividing by some other selected scaling factor.

20. A method of detecting a heartbeat rate among unwanted signals such as EMG signals and Ac hum, comprising:

sensing signals from a body using electrodes in contact with the skin of the body;

amplifying said signals while cancelling common mode noise therein;

filtering out noise below and above the frequency range in which the desired heartbeat rate will lie to generate a filtered analog signal;

converting the filtered analog signal to a plurality of digital samples;

digitally filtering the digital samples to remove further remnants of frequencies above and below the range of frequencies in which said heartbeat will lie and to suppress powerline hum at approximately 50–60 Hertz so as to generate filtered digital samples:

processing said filtered digital samples to determine said heartbeat rate;

and wherein the step of processing the filtered digital samples comprises the steps of:

comparing the amplitudes of peaks in the signal represented by the filtered digital samples to a predetermined threshold selected such that pulses in EKG complexes are usually the only pulses which have sufficient amplitude to exceed the threshold;

counting the peaks that exceed said predetermined threshold over a known time interval; and calculating the heart rate from the count and the known time interval.

21. The method of claim 20 further comprising the steps of:

using a computer to learn the approximate time when to expect each EKG complex to arrive and setting up a window around the expected time of arrival of each EKG complex so as to ignore signals received outside said window;

using a computer to learn the average amplitude of pulses inside said windows;

using a computer to use said average amplitude to calculate said predetermined threshold as some percentage of said average amplitude and using said threshold to further discriminate between EKG complexes received during said window and other pulses received during said window.

22. A method of detecting a heartbeat rate among unwanted signals such as EMG signals and Ac hum, comprising:

sensing signals from a body using electrodes in contact with the skin of the body;

amplifying said signals while cancelling common mode noise therein;

filtering out noise below and above the frequency range in which the desired heartbeat rate will lie to generate a filtered analog signal;

converting the filtered analog signal to a plurality of digital samples;

digitally filtering the digital samples to remove further remnants of frequencies above and below the range of frequencies in which said heartbeat will lie and to suppress powerline hum at approximately 50–60 Hertz so as to generate filtered digital samples; processing said filtered digital samples to determine said heartbeat rate:

and wherein the step of processing the filtered digital samples comprises:

1) using a computer to set a threshold level relative to the average amplitude of EKG complex pulses such that EKG complex pulses can be discriminated from other signals by comparison of incoming signals with said threshold and using a computer to compare incoming pulses to said threshold;

2) using a computer to subject pulses which exceed said threshold to pattern analysis to determine if the pulses are likely to be periodic;

3) for pulses which appear to be periodic, using a computer to calculate a candidate heart rate therefrom and applying rules of reason that are true for all human heart rates to said candidate heart rate to determine the confidence level that said candidate heart rate is likely to be a valid heart rate;

4) if the candidate heart rate fails any rule of reason test, using a computer to reject the candidate heart rate and start over at step 1);

5) for any candidate heart rate which passes all rule of reason tests, using a computer to determine the approximate expected time of arrival of the next EKG complex pulse and set up a window of time around said expected arrival time of each new EKG complex pulse;

6) using a computer to count only pulses that arrive during said windows and which exceed said threshold;

7) using a computer to calculate a new heart rate from the pulses detected in step 6) and applying one or more rules of reason to the new calculated heart rate to determine a level of confidence that the new calculated heart rate is a human heart rate;

8) if the new calculated heart rate fails any rule of reason, using a computer to reject it and start processing over at step 1);

9) if the new calculated heart rate passes all rules of reason, using a computer to adjust the position of said window and the level of said threshold, if necessary, based on the new calculated heart rate and the average amplitude of said pulses that exceed said threshold during said windows so as to improve the accuracy of calculation of said heart rate; and 10) periodically recalculating said heart rate, adjusting the position of said windows and said threshold level and displaying the calculated heart rate.

23. A method of detecting a heartbeat rate among unwanted signals such as EMG signals and Ac hum, comprising:

A) sensing signals from a body using electrodes in contact with the skin of the body;

B) amplifying said signals while cancelling common mode noise therein;

C) filtering out noise below and above the frequency range in which the desired heartbeat rate will lie to generate a filtered analog signal;

D) converting the filtered analog signal to a plurality of digital samples;

E) digitally filtering the digital samples to remove further remnants of frequencies above and below the range of frequencies in which said heartbeat will lie and to suppress powerline hum at approximately 50–60 Hertz so as to generate filtered digital samples:

F) processing said filtered digital samples to determine said heartbeat rate; and wherein the step of processing the filtered digital samples comprises:

1) using a computer to enhance said filtered digital samples to improve the contrast between EKG complexes and noise or other artifact signals and generate enhanced digital samples;

2) using a computer to compare pulses represented by said enhanced digital samples to a threshold and determine from pulses which exceed said threshold in amplitude whether any three consecutive pulses seem to be periodic and represent a reasonable human heart rate within a range from about 30 beats per minute to about 220 beats per minute;

3) if three consecutive pulses are found which appear to be periodic and represent a possible human heart rate, using a computer to calculate from the shape and amplitude of said three consecutive pulses in EKG complexes a logic template comprising a two dimensional array of logic 1's and 0's which represent the shape and amplitude of the three consecutive pulses, said logic template for use in said enhancing step by cross-correlation of the shapes and amplitudes of new pulses in said filtered digital samples with said logic template and using said results of said cross-correlation as said enhanced digital samples and then repeating the process of step 2) to determine if any new pulse or pulses in EKG complexes are detected using the new logic template to enhance the digital data, said new pulse or pulses appearing to be periodic among themselves or relative to the three consecutive beats previously detected;

4) using a computer to determine the heart rate of the new pulse in EKG complexes detected using the new logic template relative to the three consecutive pulses in EKG complexes previously detected or the heart rate represented by the string of EKG pulses newly detected using the new logic template, and comparing the new heart rate to the heart rate of the three consecutive pulses in EKG complexes previously detected, and determining if the new heart rate is sufficiently close to the old heart rate to physically make sense since a human heart rate cannot change faster than a predetermined rate;

5) if the new heart rate does not make sense relative to the old heart rate, using a computer to reject the new heart rate and return to step 1) to start screening new incoming data using the new logic template;

6) if 5 intervals pass when new pulses in EKG complexes would be expected to arrive based upon the newly calculated heart rate, but no pulse appears in the enhanced digital sample data that exceed the threshold in any of these 5 intervals, using a computer to reject the new logic template and returning to step A;

7) if the new heart rate is sufficiently close to the old heart rate to generate a sufficiently high level of confidence that the new heart rate is valid, using a computer to average the new heart rate with the old heart rate and display the result.

24. A method of detecting a heartbeat rate among unwanted signals such as EMG signals and Ac hum, comprising:

A) sensing signals from a body using electrodes in contact with the skin of the body;

B) amplifying said signals while cancelling common mode noise therein;

C) filtering out noise below and above the frequency range in which the desired heartbeat rate will lie to generate a filtered analog signal;

D) converting the filtered analog signal to a plurality of digital samples;

E) digitally filtering the digital samples to remove further remnants of frequencies above and below the range of frequencies in which said heartbeat will lie and to suppress powerline hum at approximately 50–60 Hertz so as to generate filtered digital samples;

F) processing said filtered digital samples to determine said heartbeat rate; and wherein the step of processing the filtered digital samples comprises the steps:

1) using a computer to learn and record the characteristics of the EKG complex signals being processed;

2) using a computer and the learned characteristics of the EKG complex signals being processed to analyzing incoming filtered digital data samples to select EKG complexes therefrom;

3) if 5–10 seconds have elapsed without a new heartbeat pulse in an EKG complex being detected, using a computer to determine if a signal has been received from a user indicating heart rate calculation is still desired;

4) if not, discontinuing the process of attempting to determine a heart rate; and 5) if so, repeating steps A through E and steps 1) through 5).

* * * * *